United States Patent [19] [11] Patent Number: 6,085,153
Hirsh et al. [45] Date of Patent: Jul. 4, 2000

[54] DIFFERENTIAL SPECTRAL TOPOGRAPHIC ANALYSIS (DISTA)

[75] Inventors: Allen G Hirsh, Silver Spring; Latchezar I. Tsonev; Serguei Litvinovitch, both of Gaithersburg; Patrick M. Mehl, North Potomac, all of Md.

[73] Assignee: Henry M. Jackson Foundation, Rockville, Md.

[21] Appl. No.: 08/964,204

[22] Filed: Nov. 4, 1997

Related U.S. Application Data

[60] Provisional application No. 60/030,454, Nov. 6, 1996.

[51] Int. Cl.[7] ........................................... G06F 19/00
[52] U.S. Cl. ........................ 702/23; 702/27; 702/30; 356/326; 356/327
[58] Field of Search ................................. 702/22–23, 27, 702/30, 32; 356/326, 327, 346

[56] References Cited

U.S. PATENT DOCUMENTS

| 4,267,572 | 5/1981 | Witte | 702/23 |
| 4,642,778 | 2/1987 | Hieftje et al. | 702/23 |
| 4,885,697 | 12/1989 | Hubner | 702/27 |
| 5,446,681 | 8/1995 | Gethner et al. | 702/27 |
| 5,481,476 | 1/1996 | Windig | 702/23 |
| 5,612,783 | 3/1997 | Hirsh | 356/327 |

FOREIGN PATENT DOCUMENTS

| 63-229350 | 9/1988 | Japan | G01N 23/22 |

*Primary Examiner*—Marc S. Hoff
*Assistant Examiner*—Bryan Bui
*Attorney, Agent, or Firm*—Finnegan, Henderson, Farabow, Garrett & Dunner, L.L.P.

[57] ABSTRACT

The present invention provides a new analysis based on Differential Spectral Topographic Analysis (DISTA). Using data from the spectral methods known in the art, DISTA is based upon the normalization of the spectra to a fixed topographic space, creating a set of spectral forms, and the summation of the absolute differences in topography between one or more reference spectra and the test spectra taken at different magnitudes of the perturbing parameter. This method allows for a sensitive estimate of the fraction of form A and form B of an entity of interest. This method also allows for the calculation of apparent free energy from the conversion of the entity of interest from a first to a second form where appropriate, and in the alternative, calculation of a fraction of structural changes.

25 Claims, 23 Drawing Sheets

(20 of 23 Drawing Sheet(s) Filed in Color)

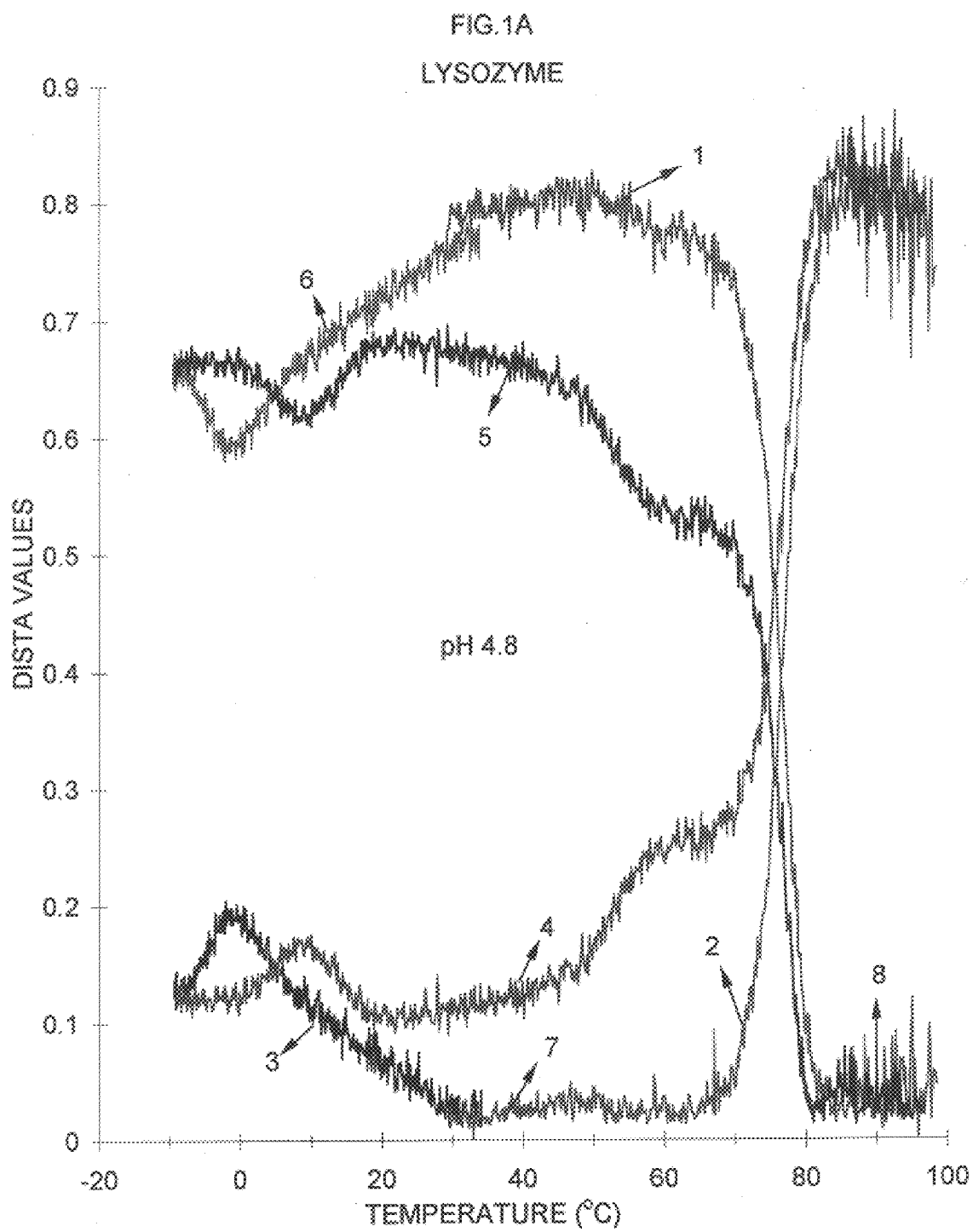

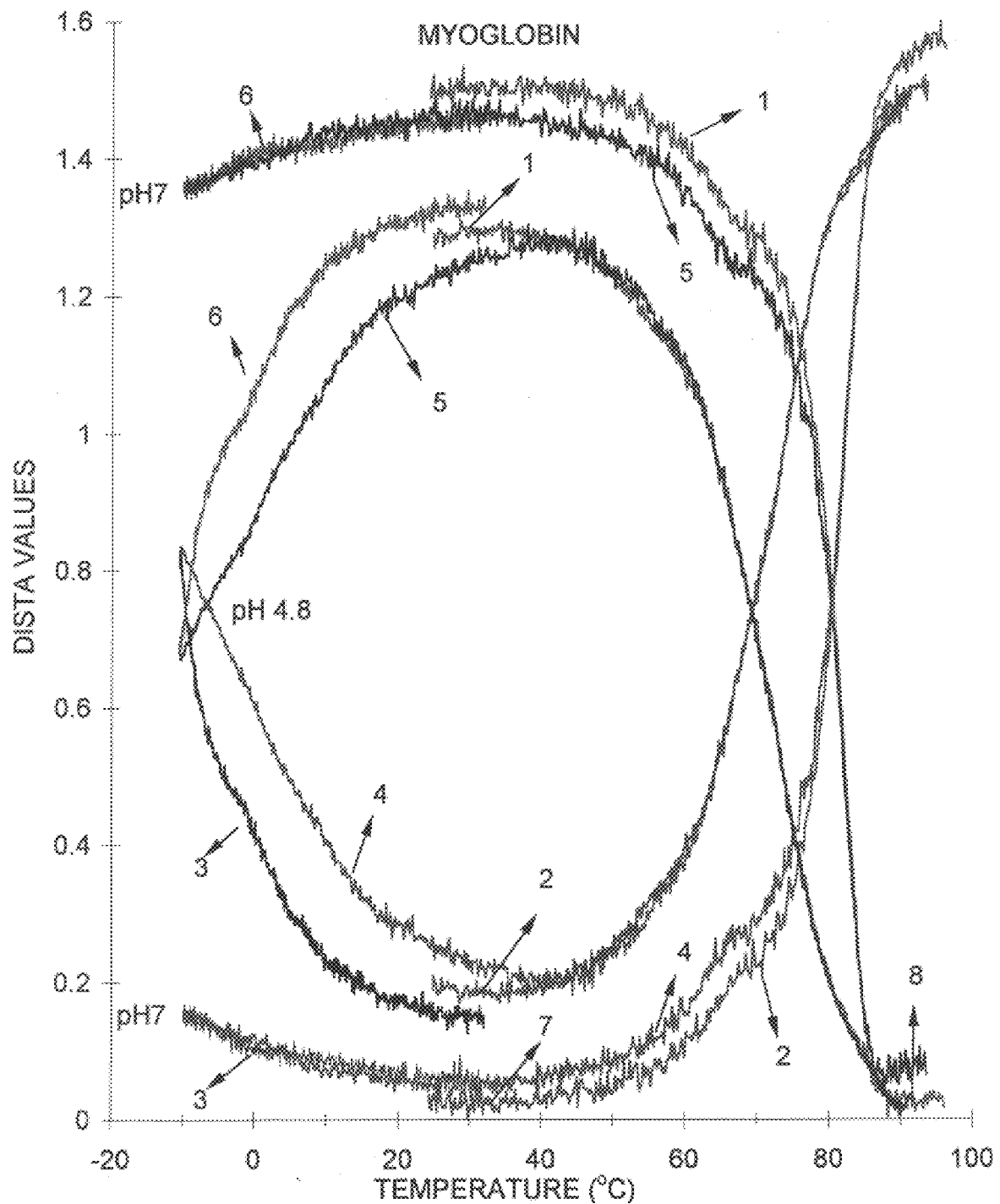

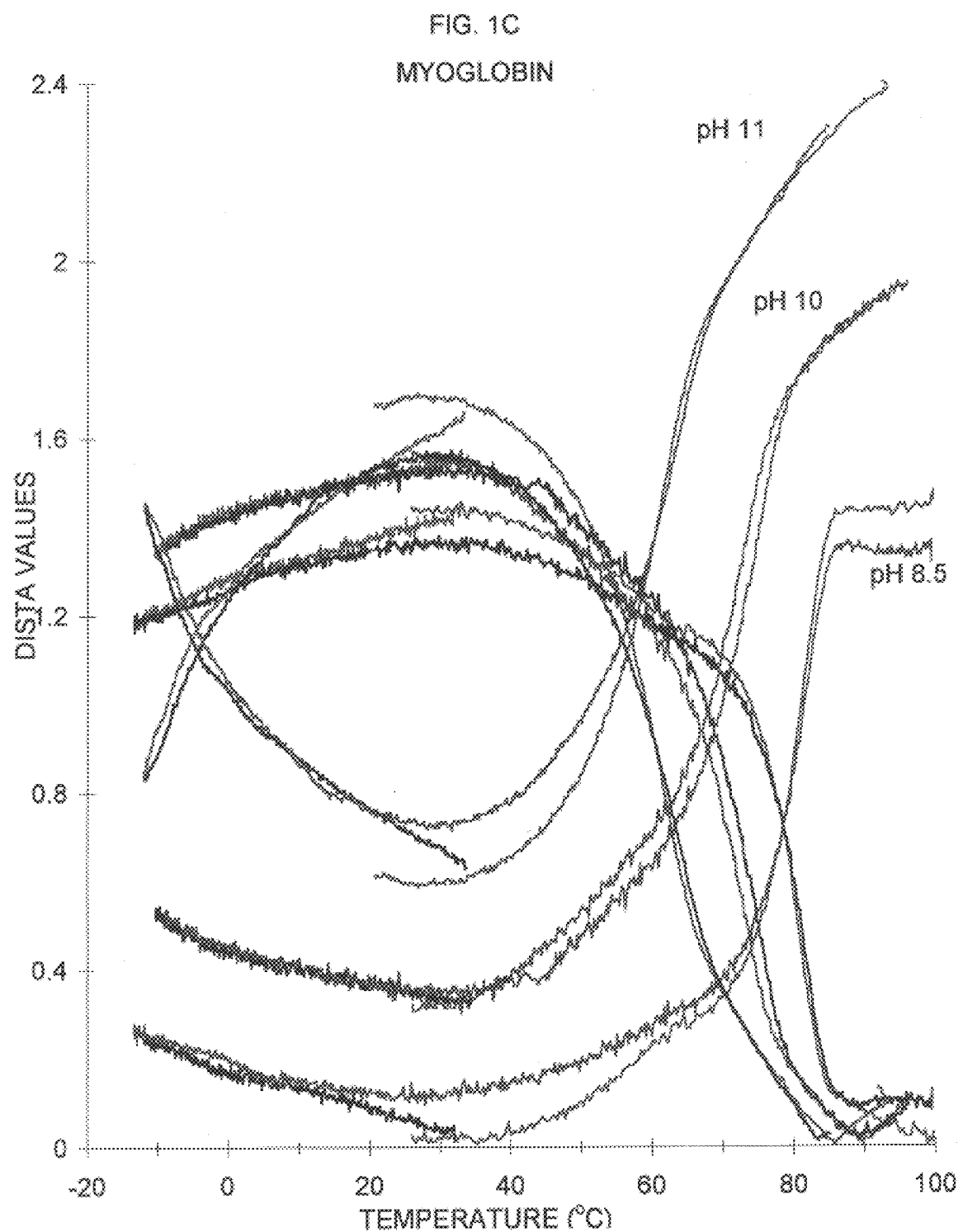

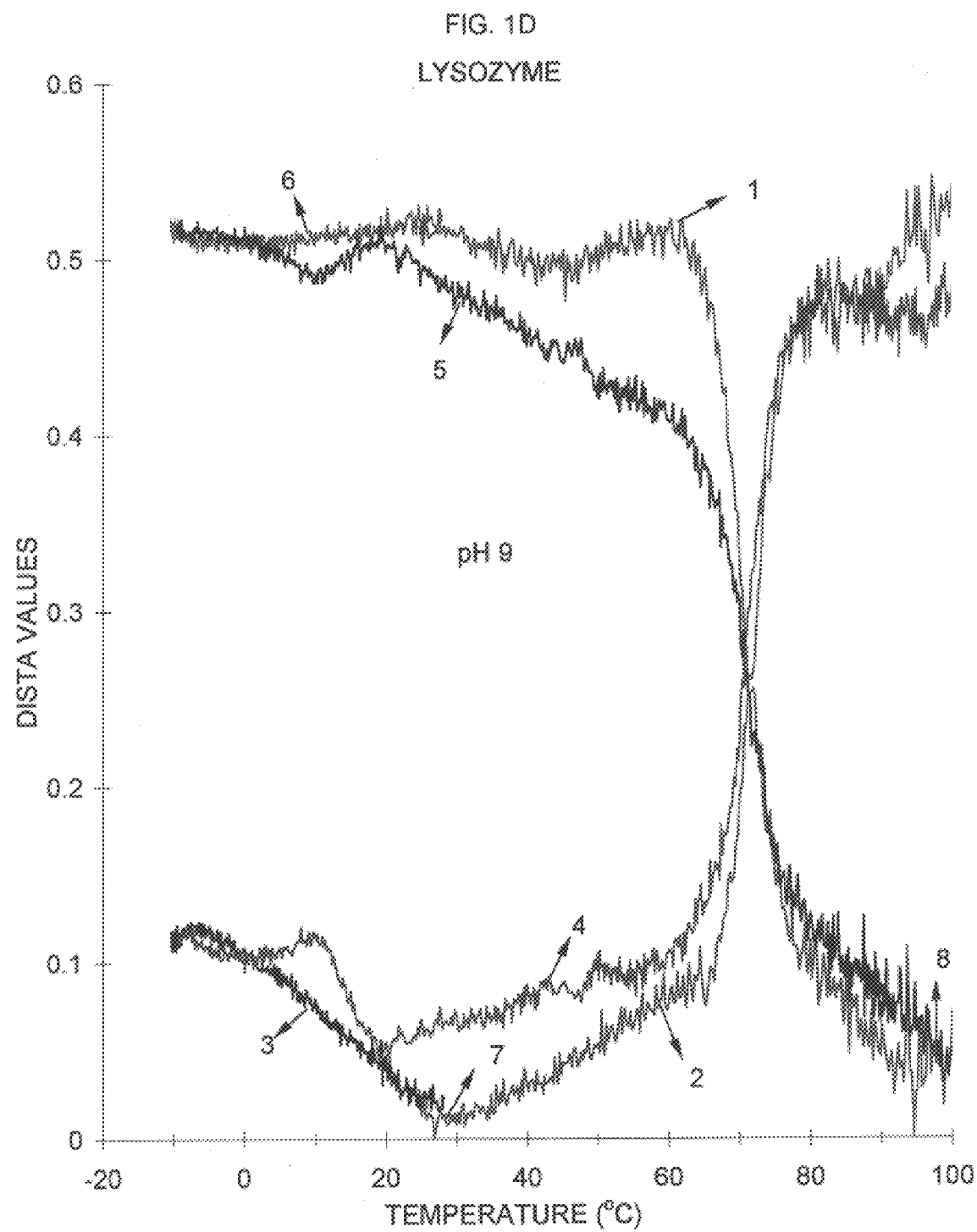

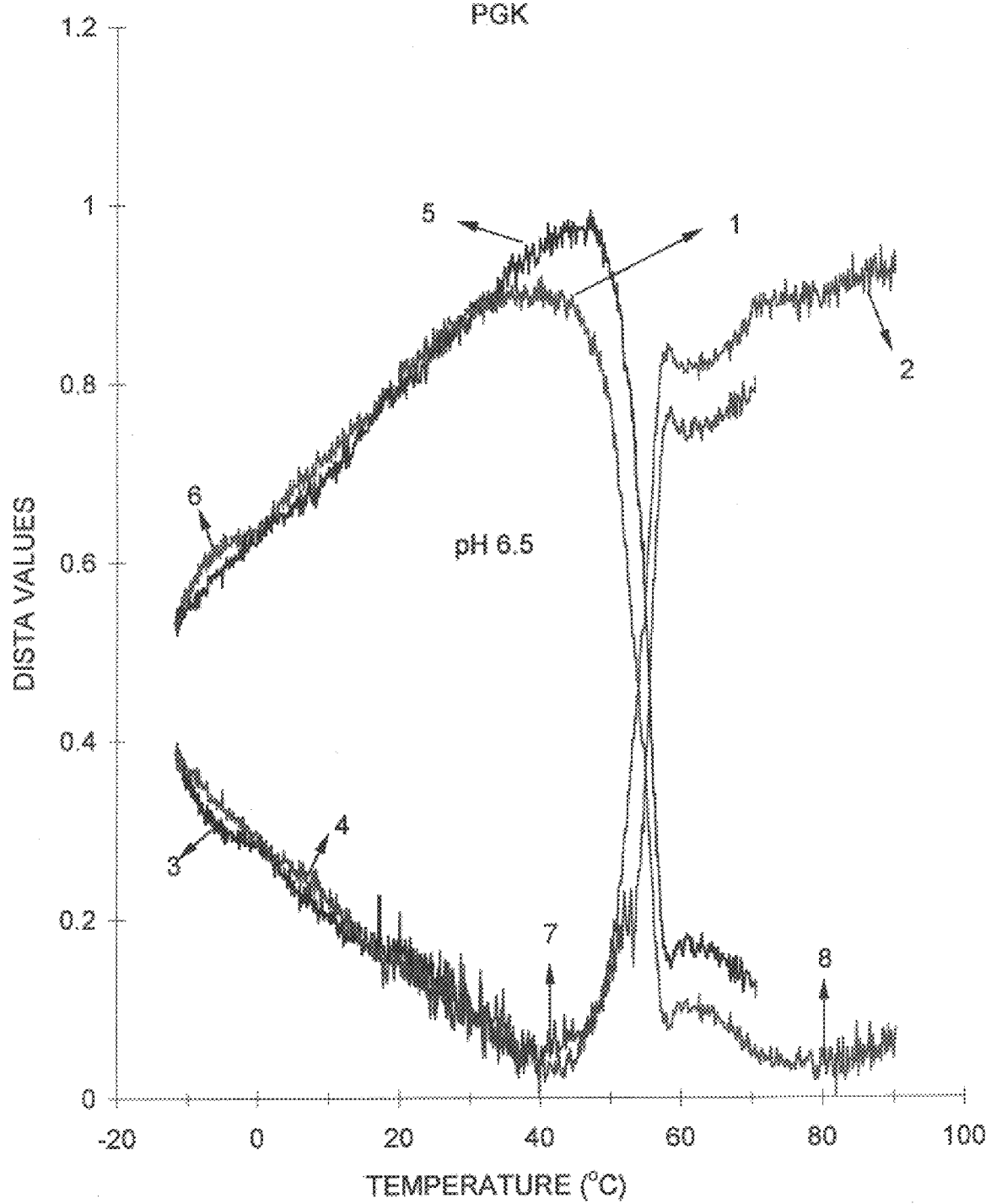

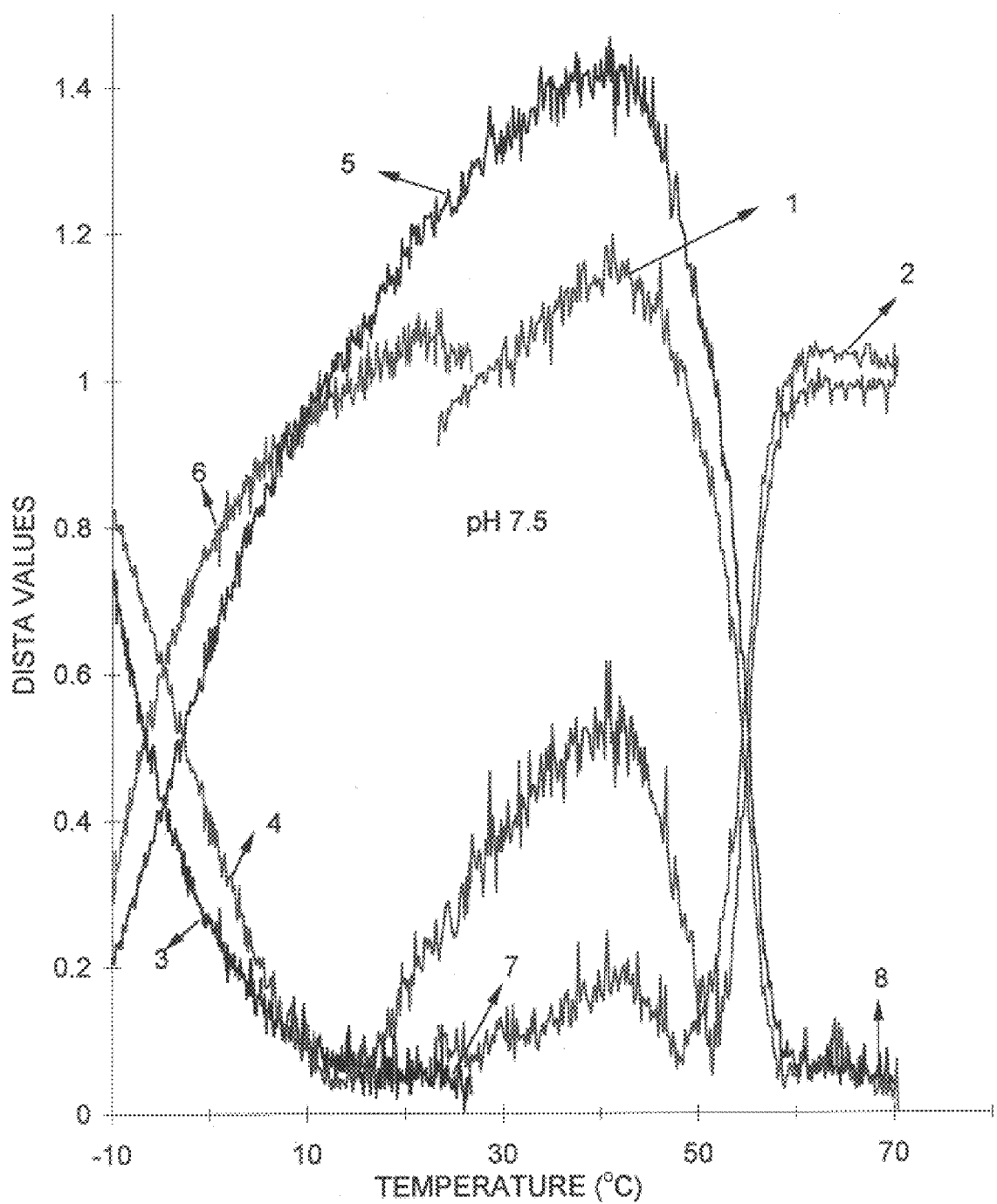

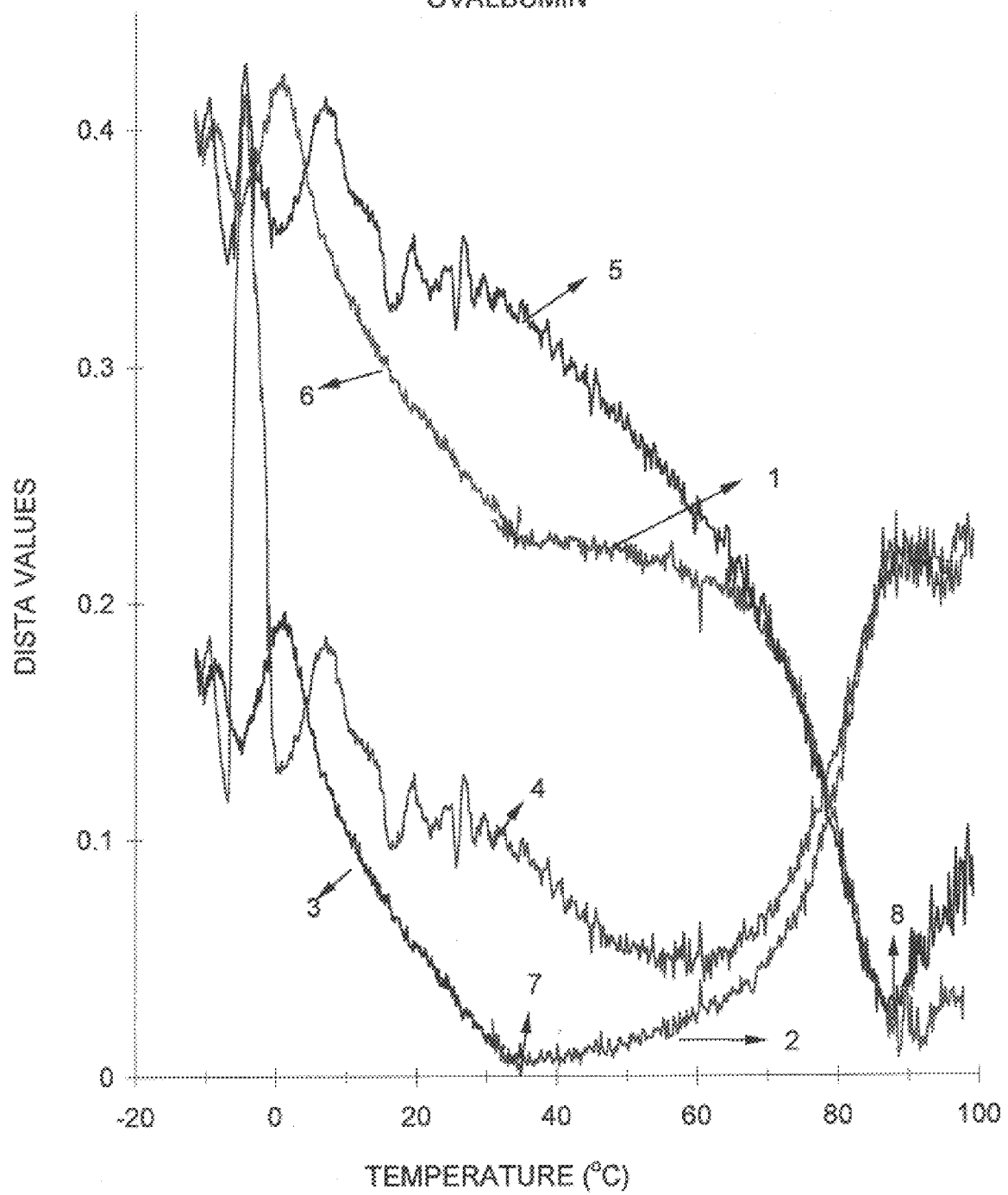

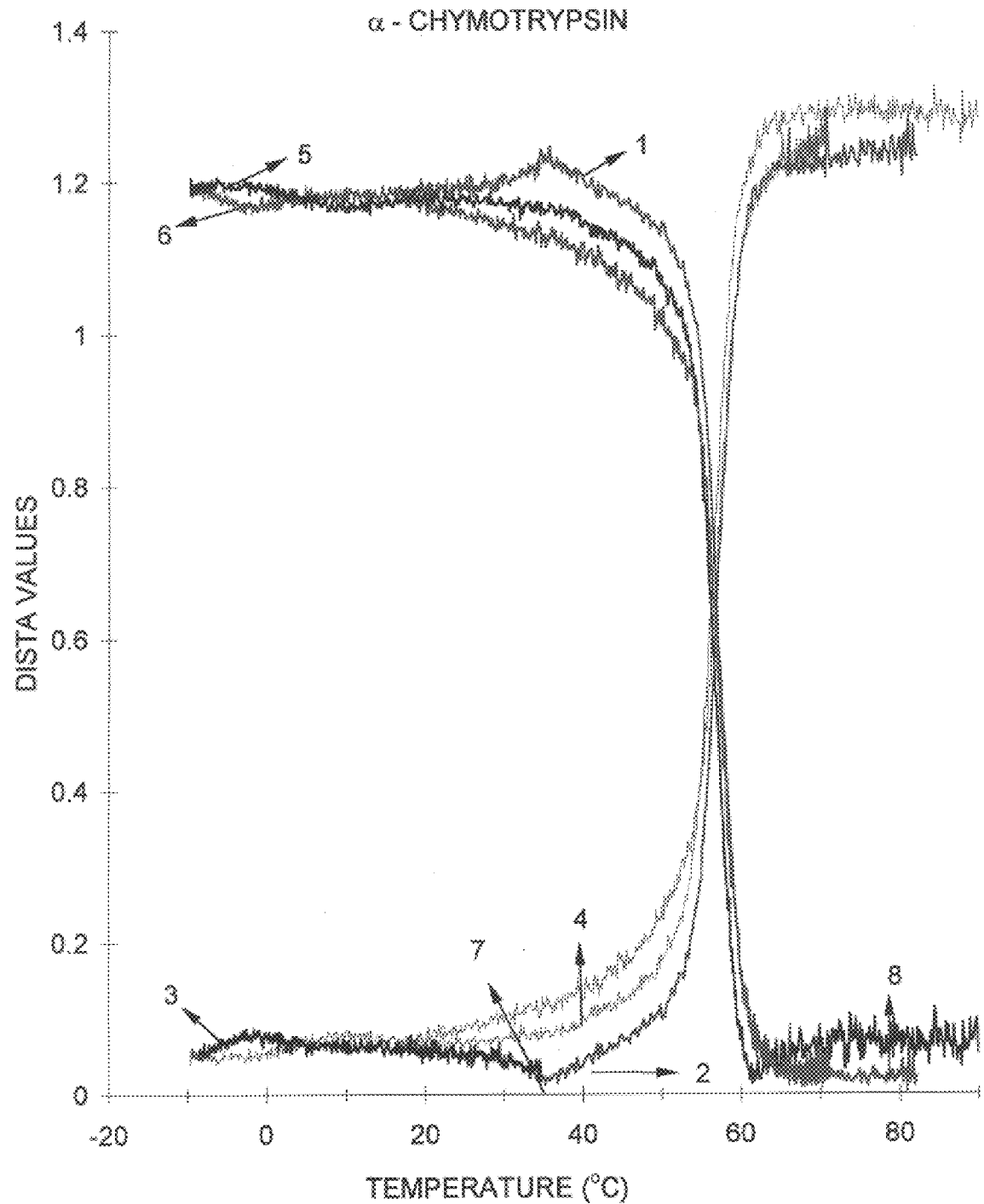

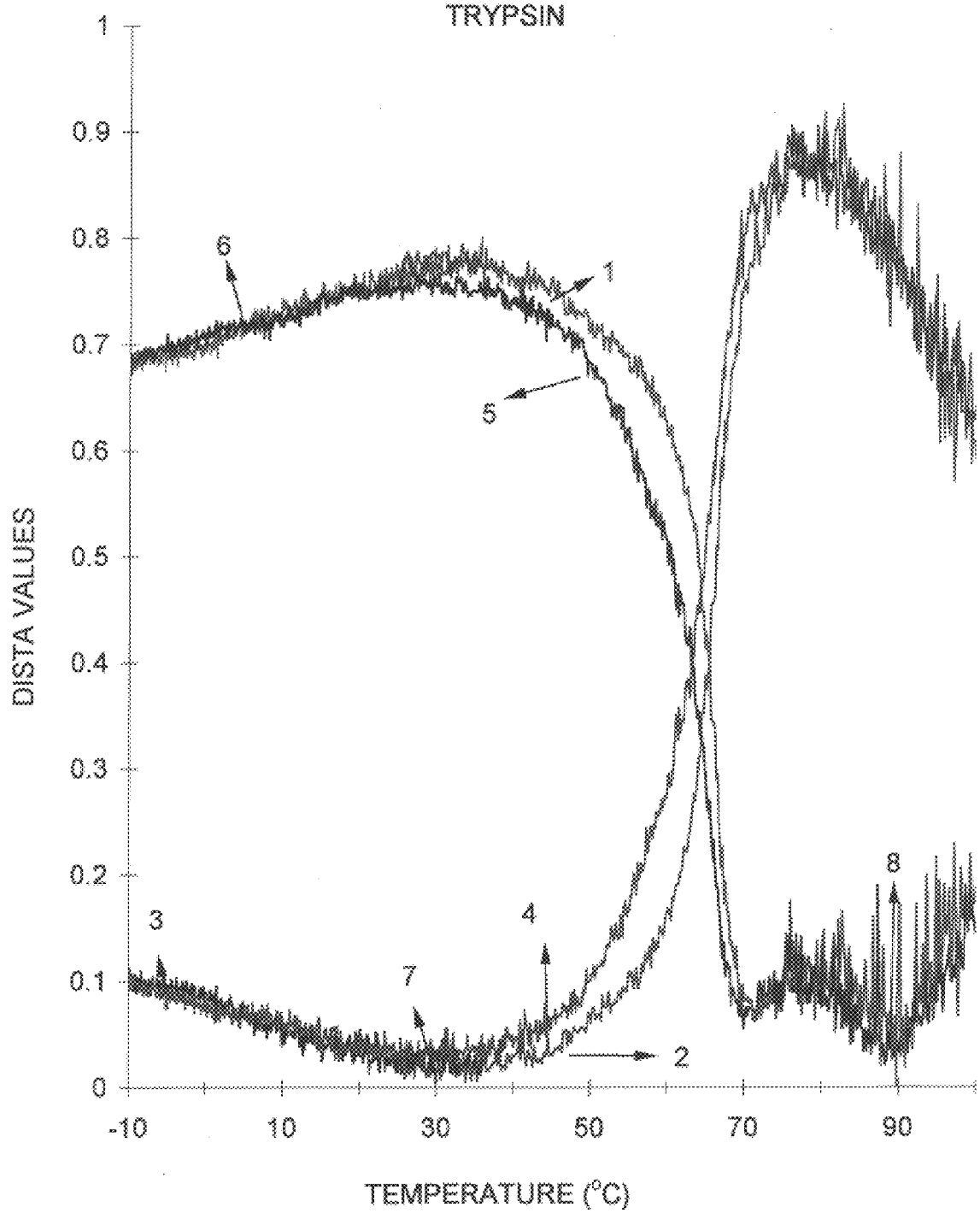

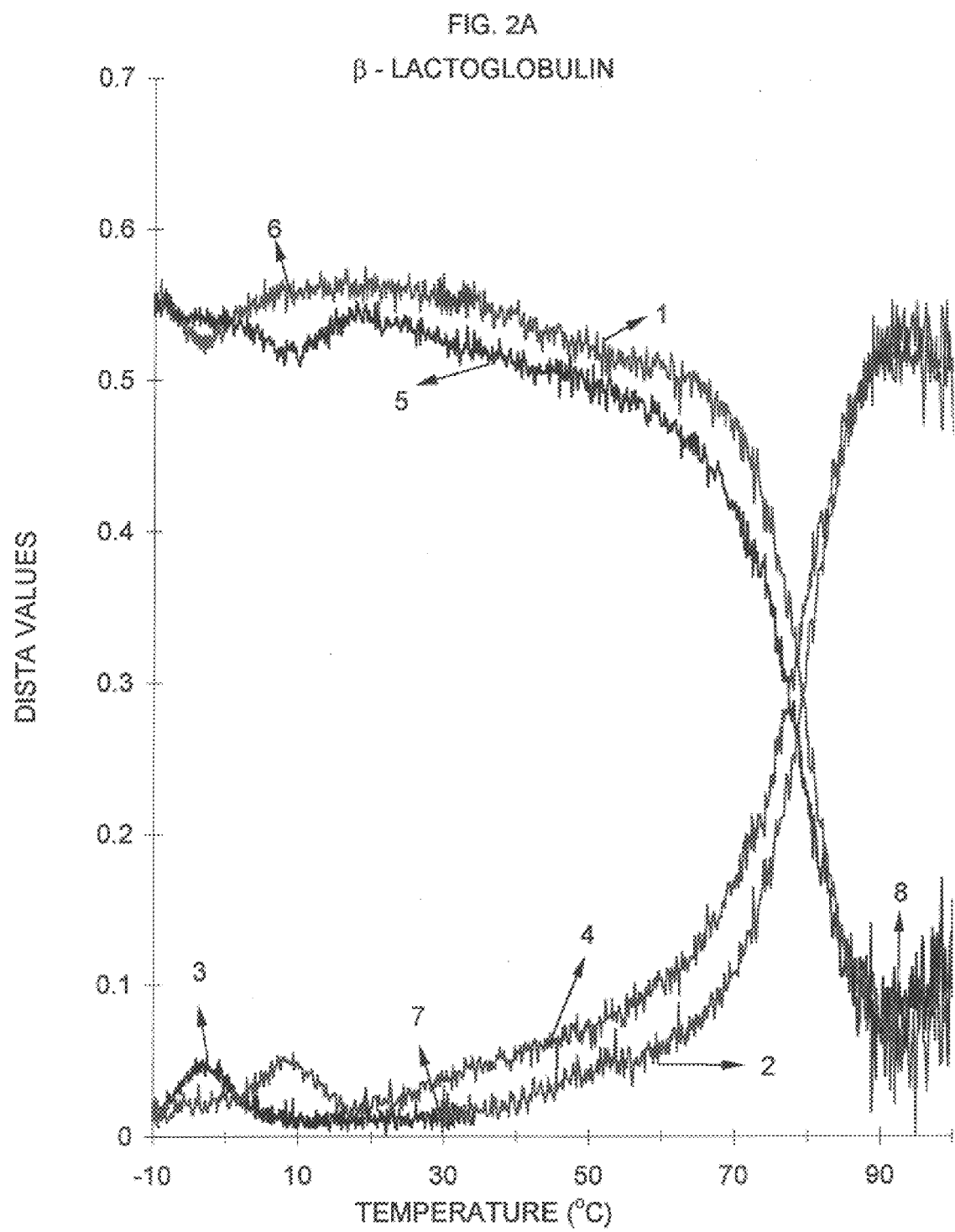

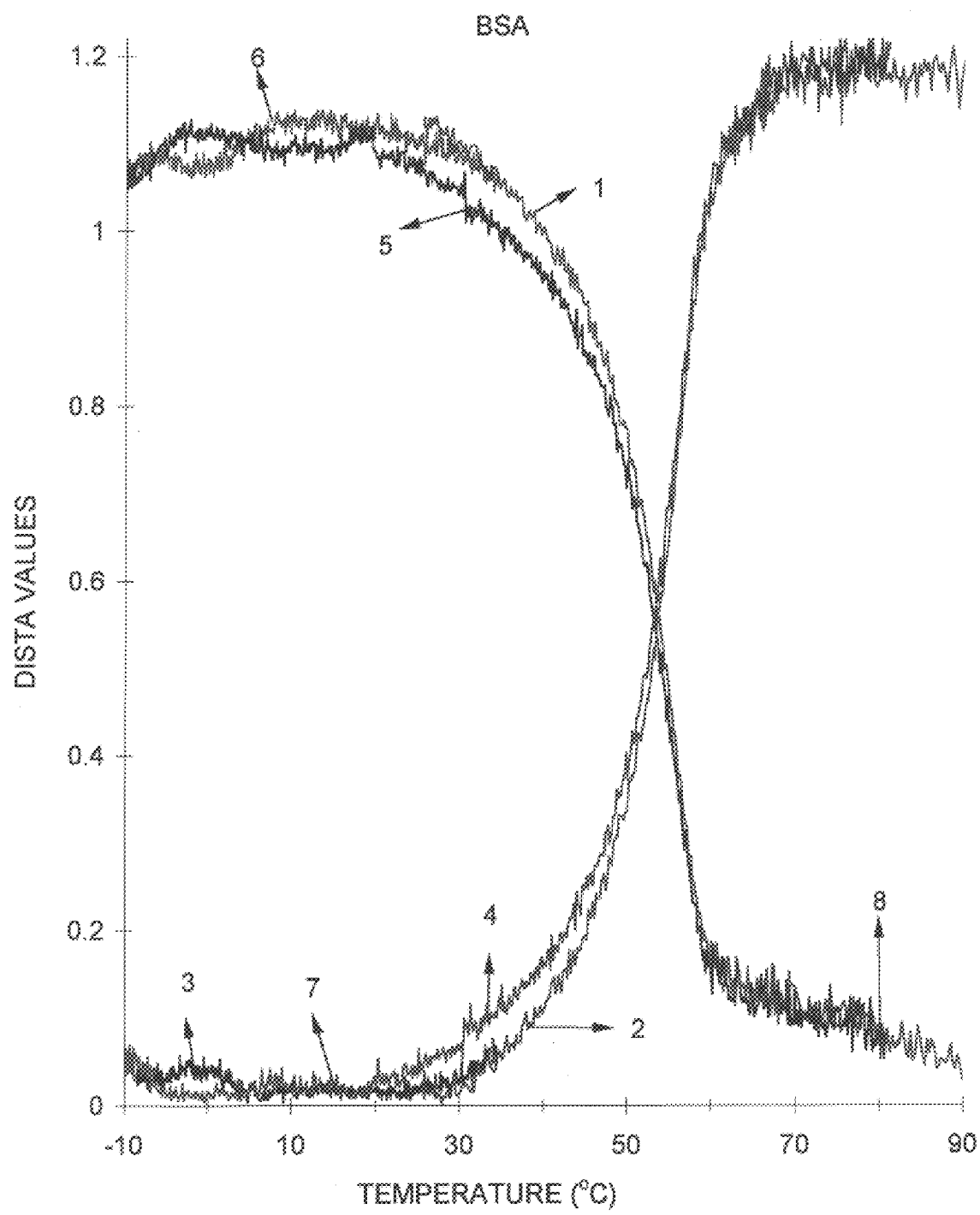

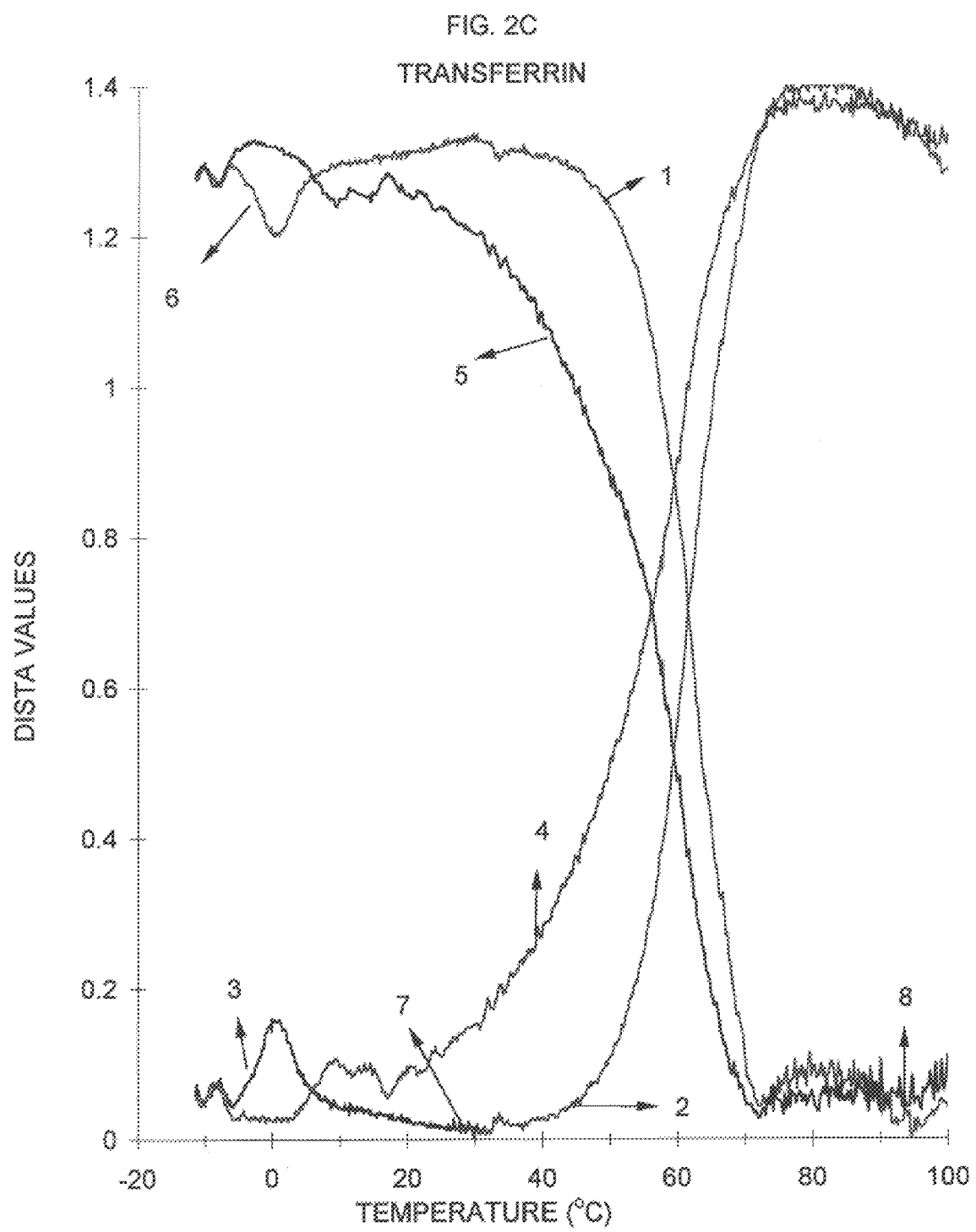

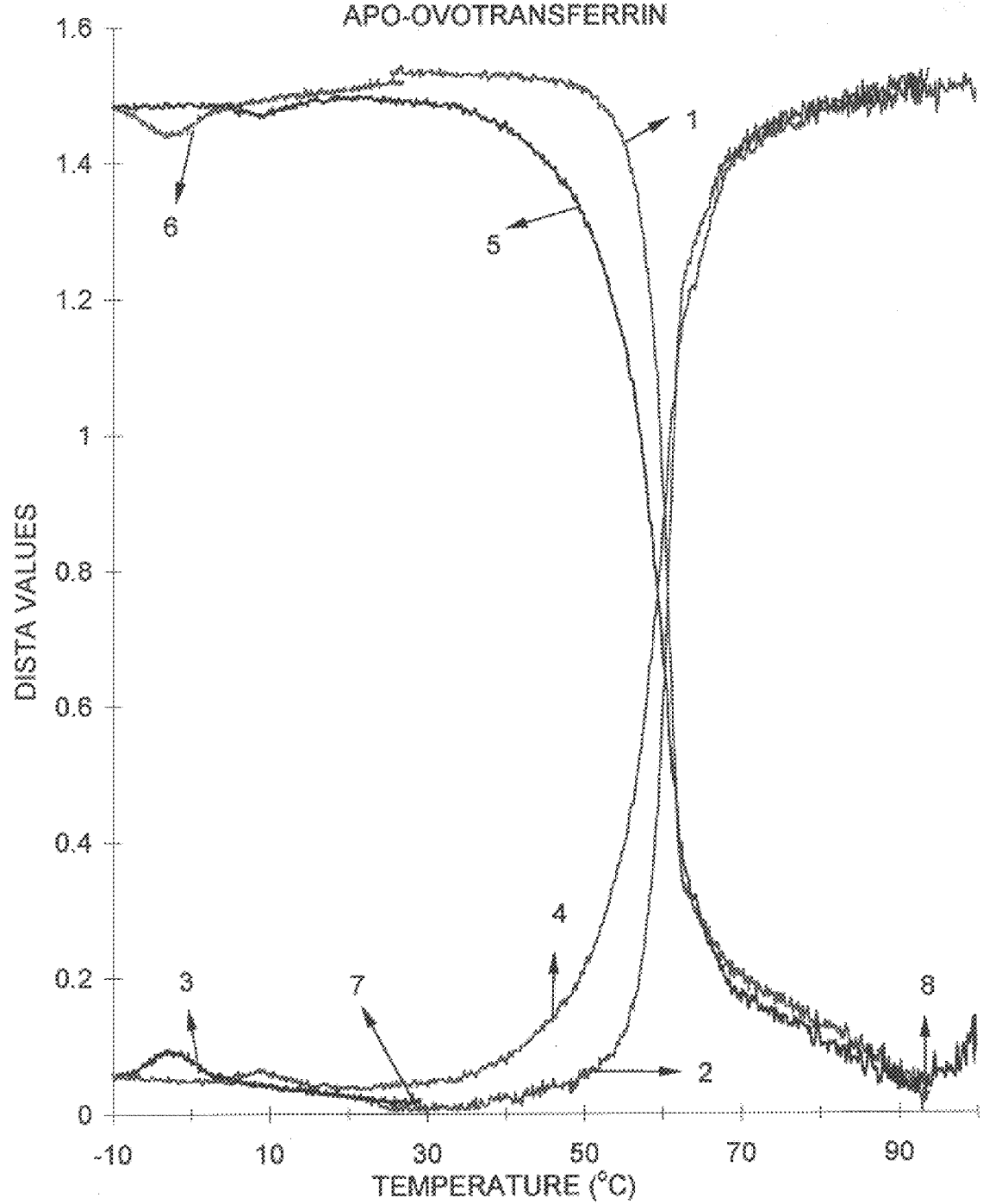

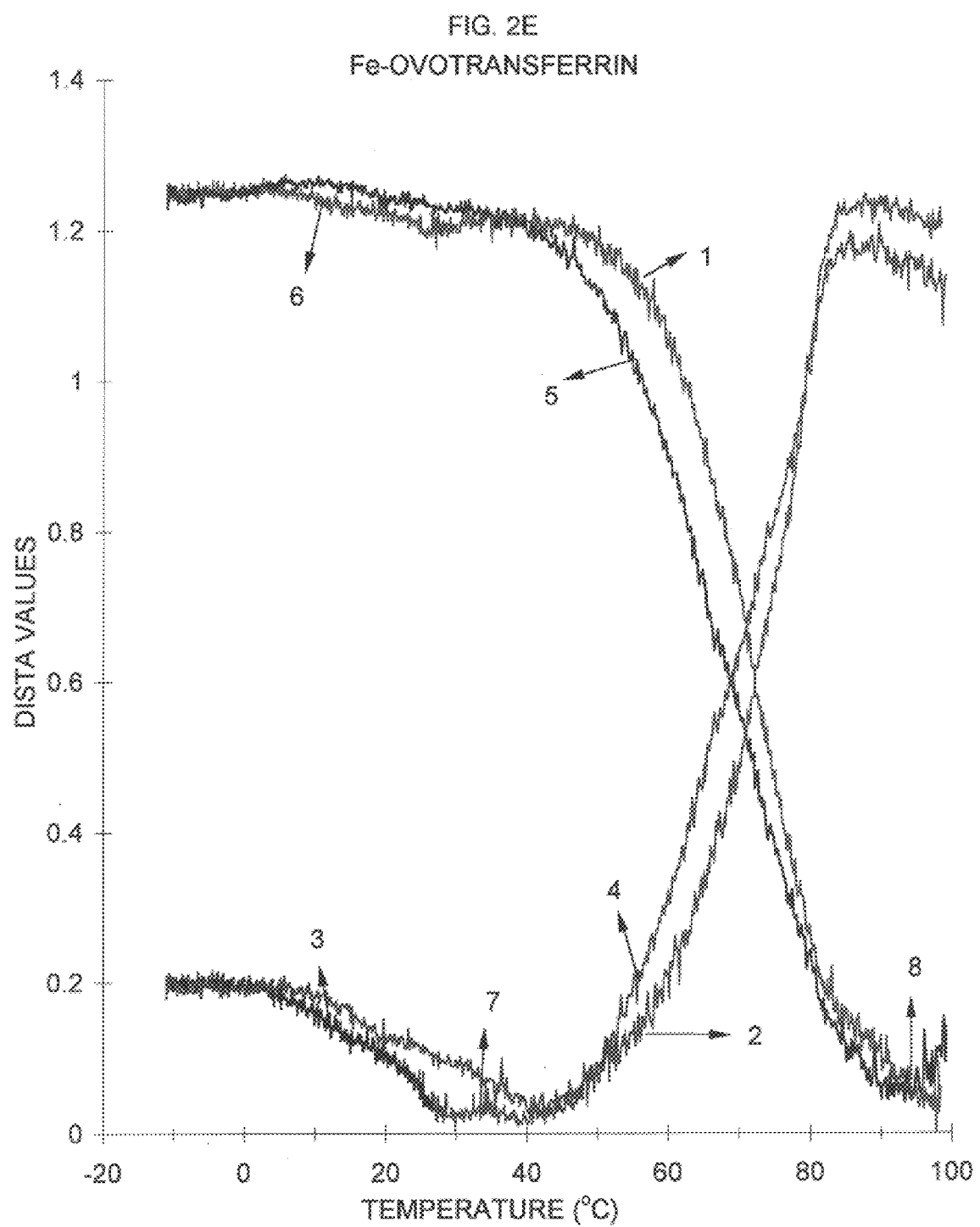

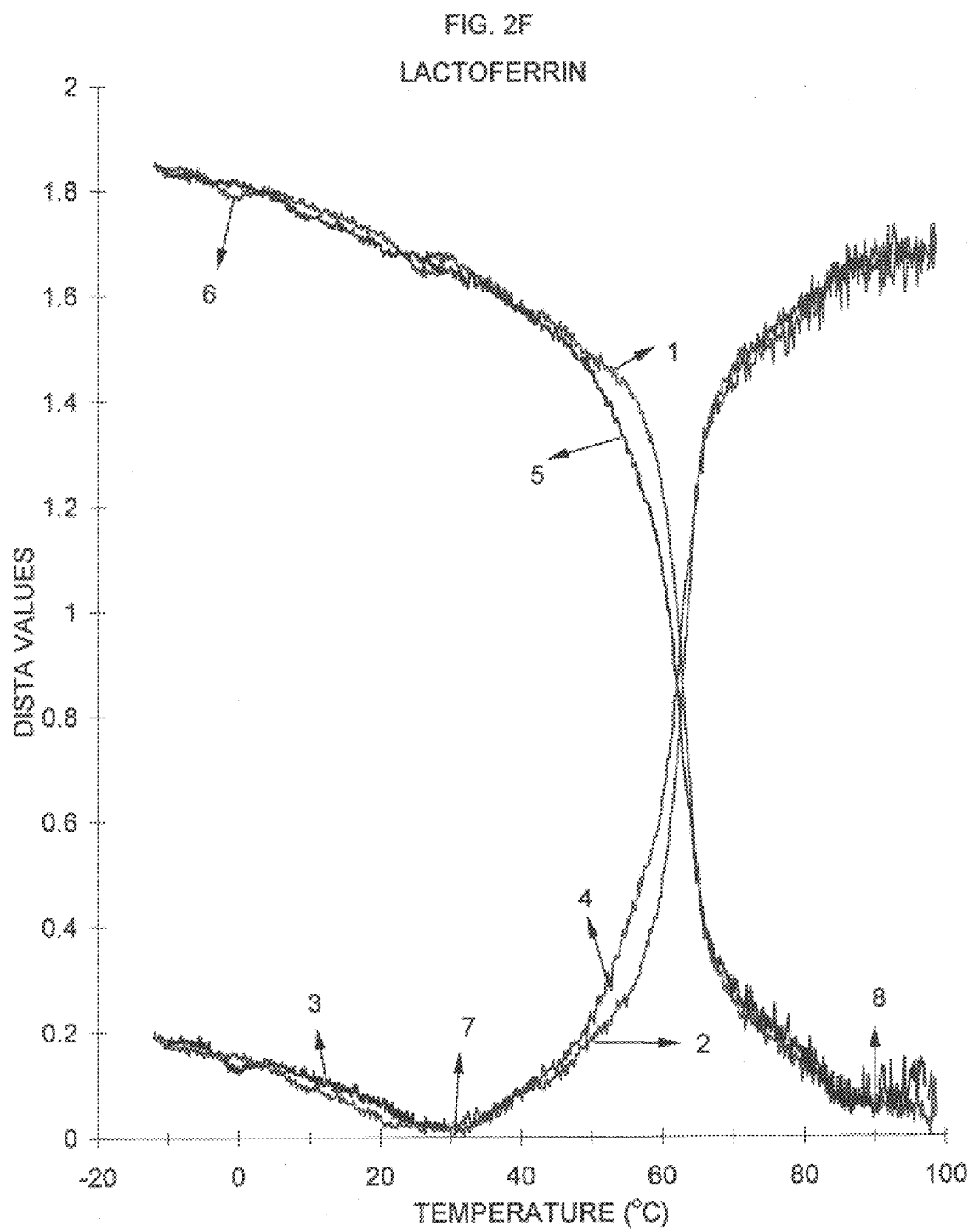

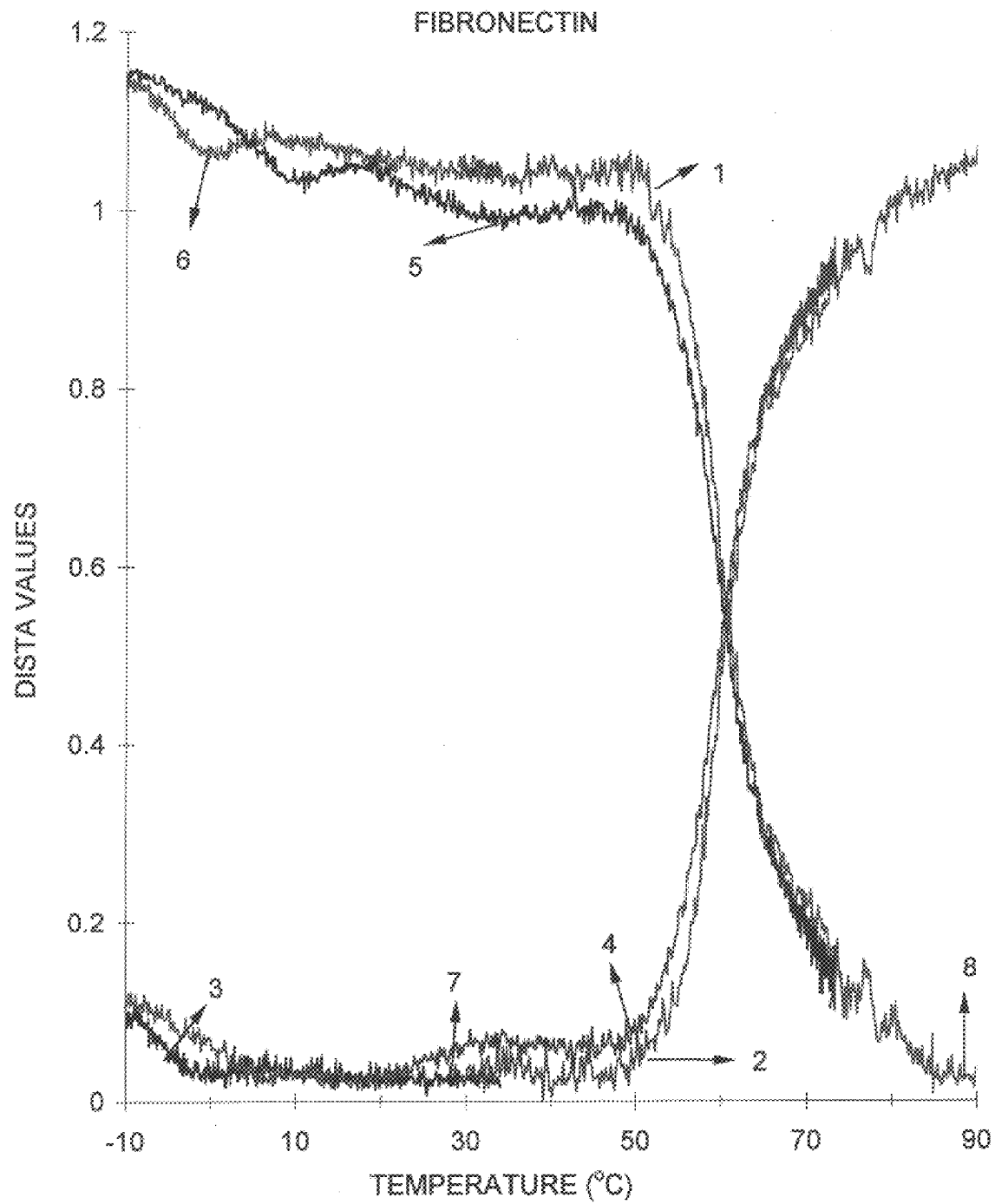

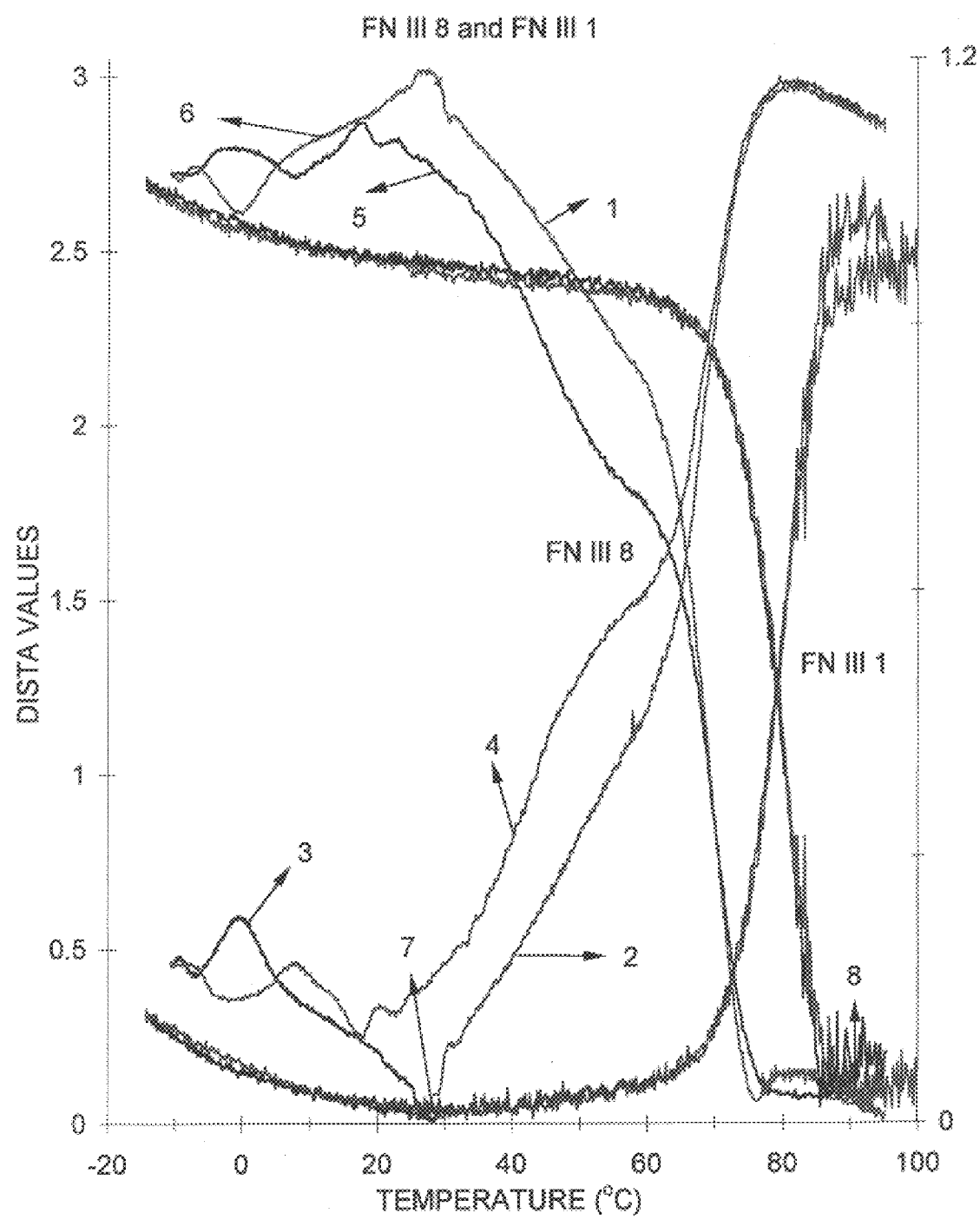

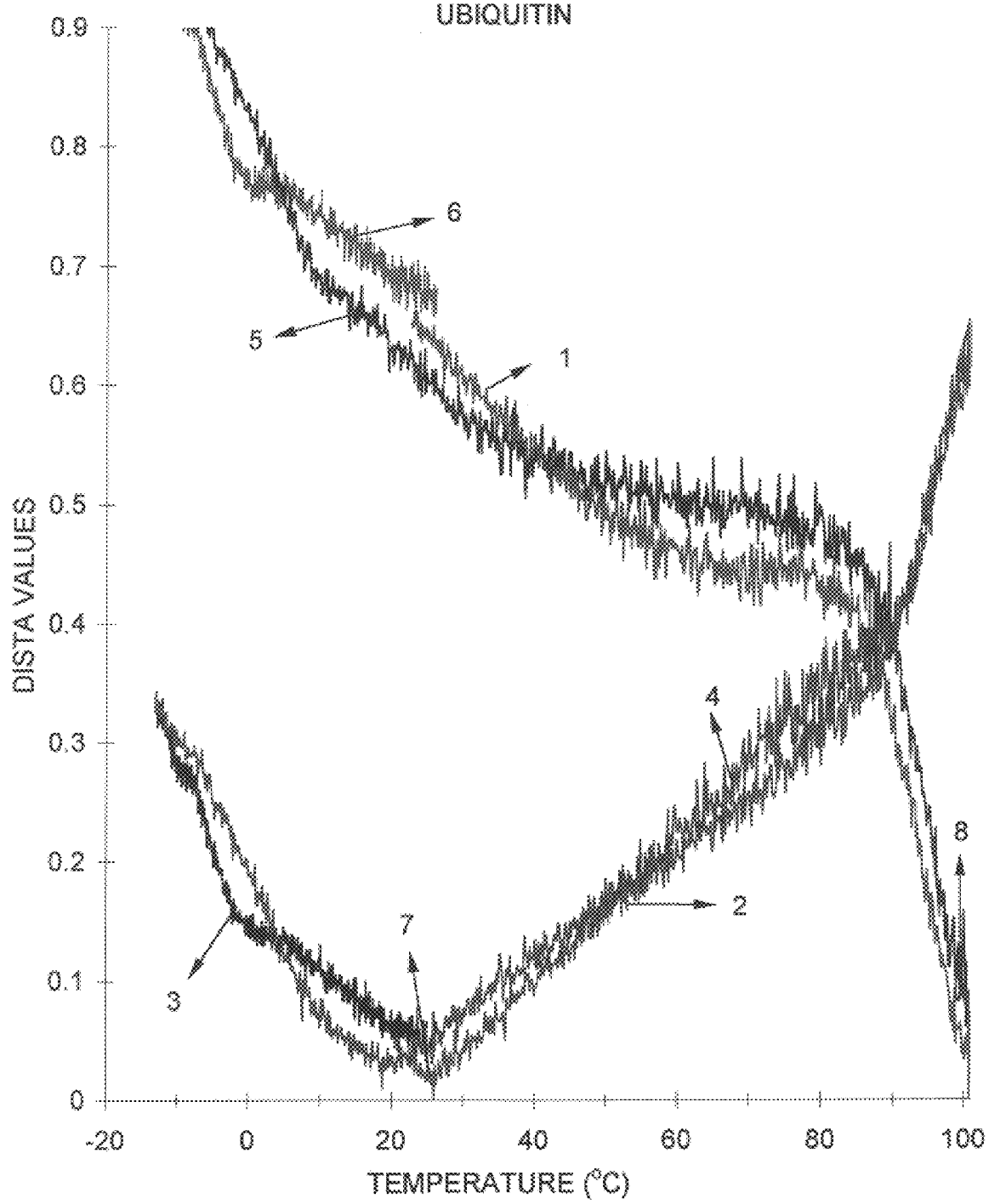

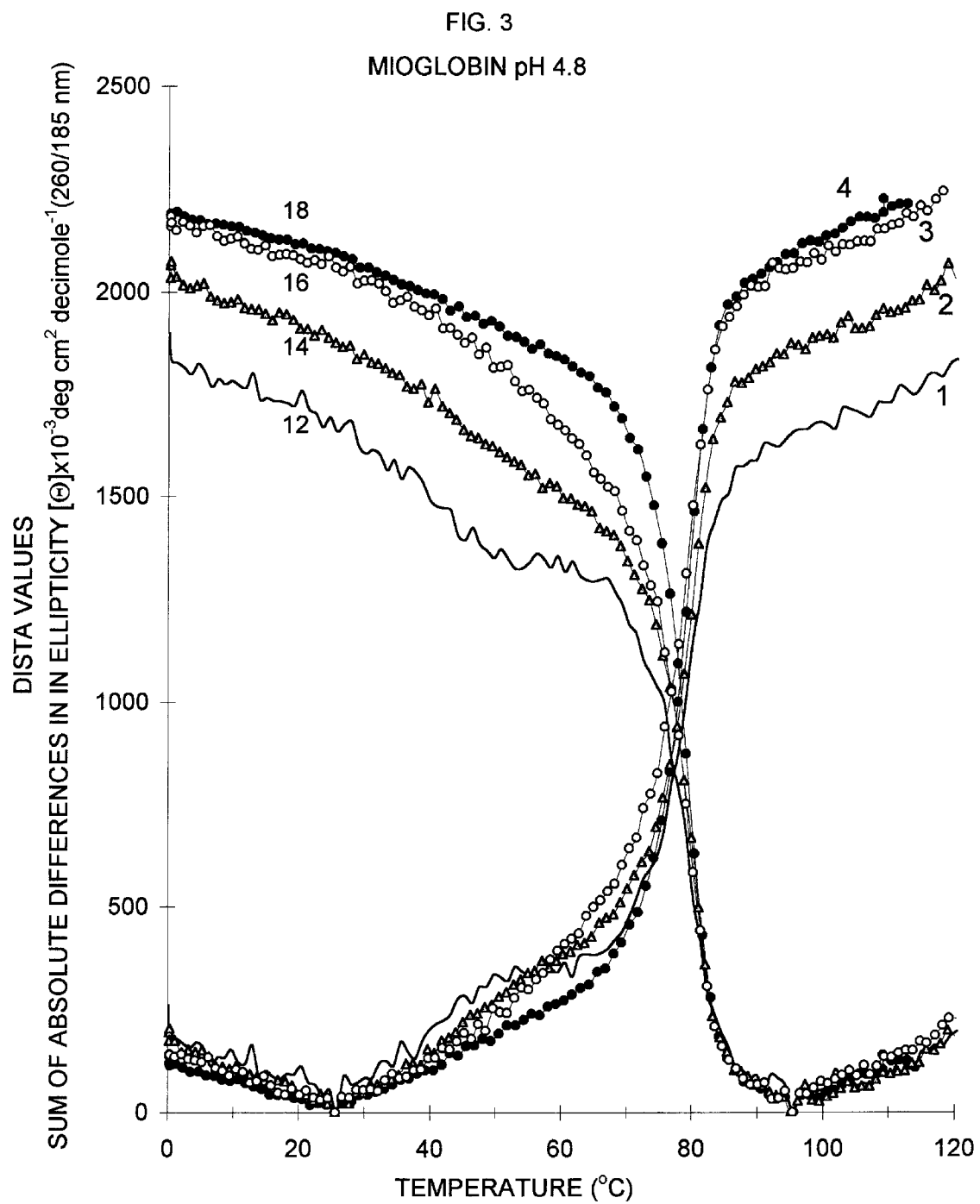

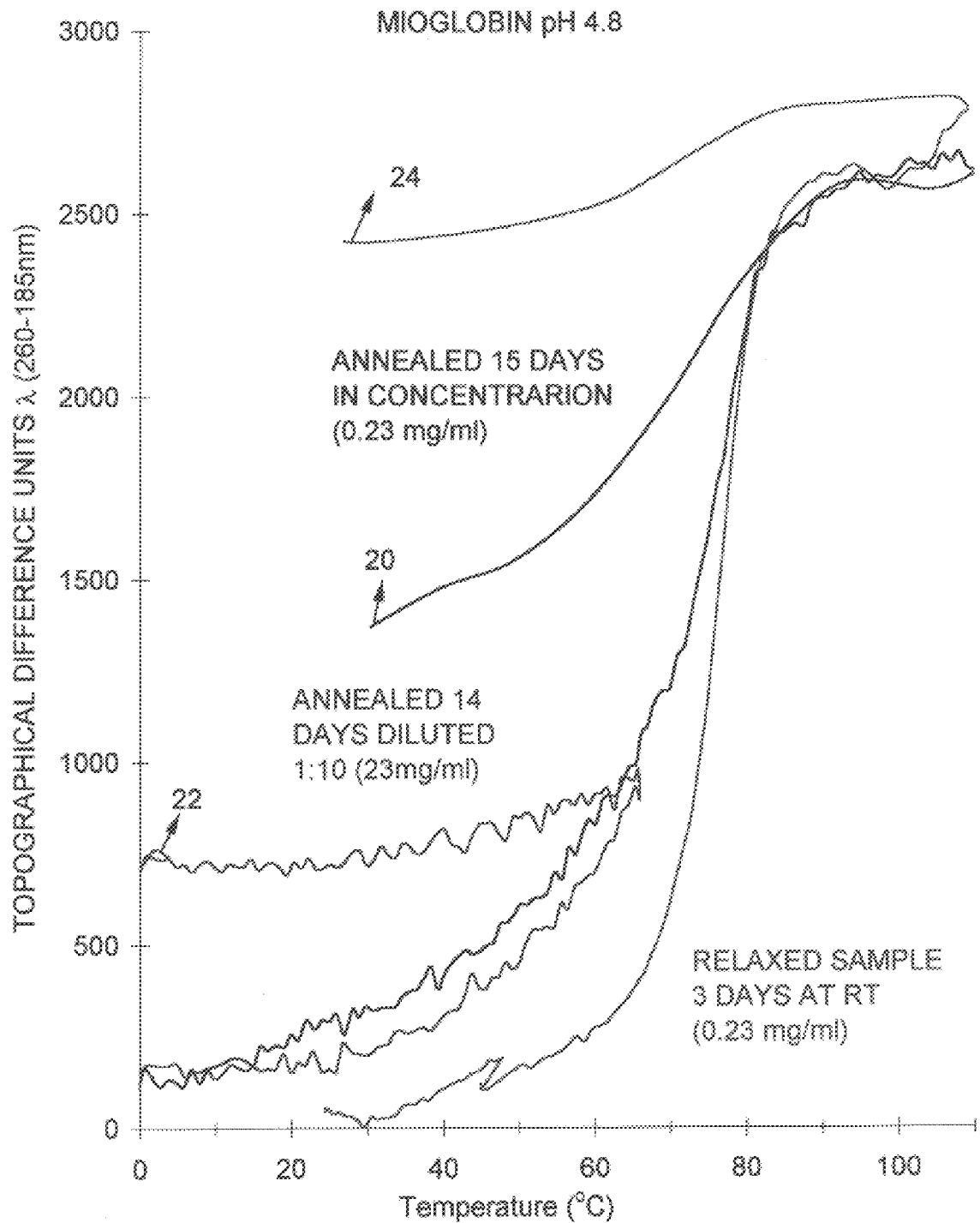

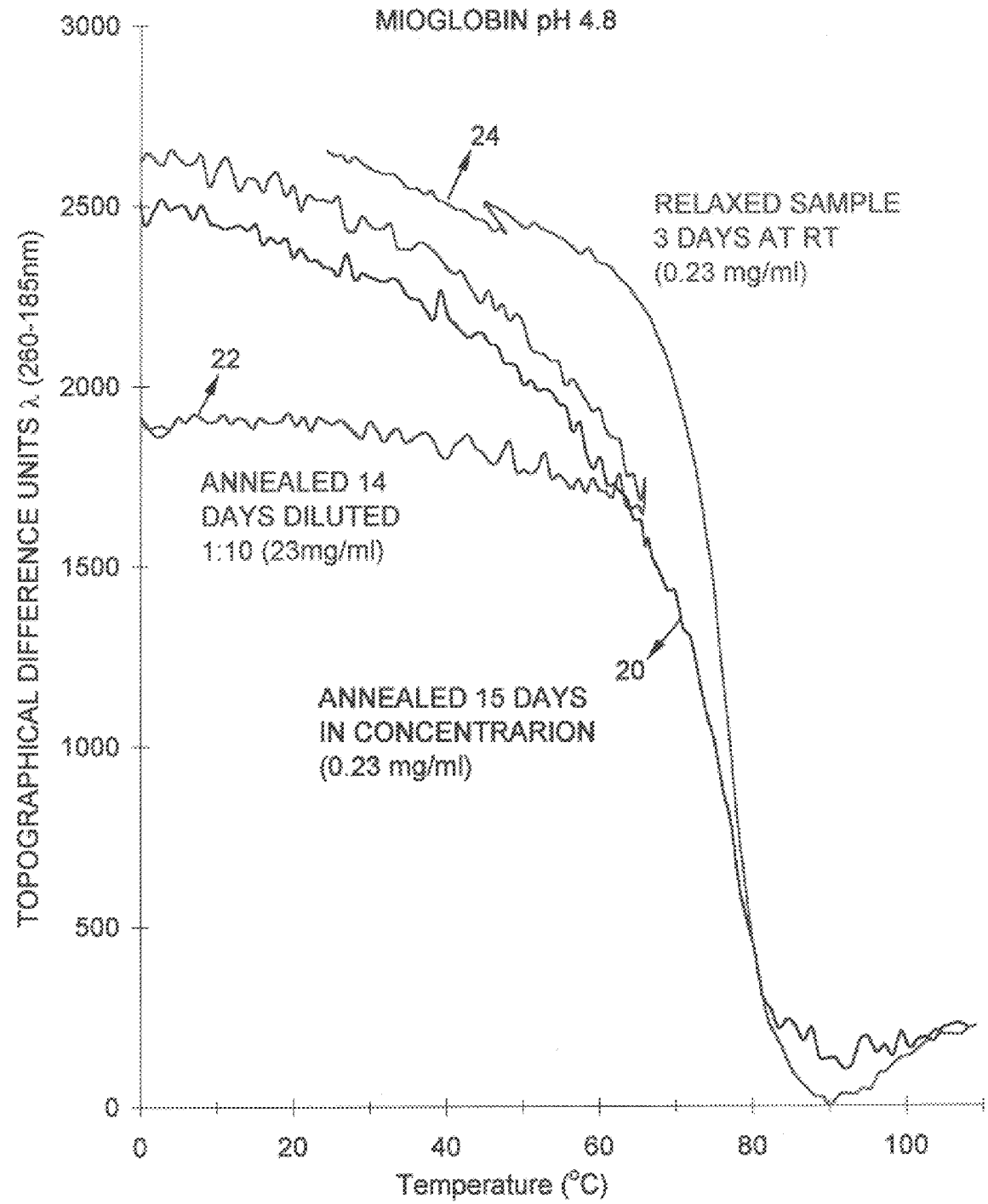

DIFFERENTIAL SPECTRAL TOPOGRAPHIC ANALYSIS (DISTA)

This application claims all benefits of United States Provisional Application Number 60/030,454, filed Nov. 6, 1996.

GOVERNMENT INTEREST

The invention described herein may be manufactured, licensed, and used for United States governmental purposes without the payment of any royalties to the inventors or assignee.

BACKGROUND OF INVENTION

1. Field of Invention

This invention relates to a new method of spectroscopic analysis to determine the fraction of conversion of a physical configuration of a system of interest from a first configuration to a second configuration, and in particular, a method to determine respective fractions of two different forms of a molecule in solution. It has broad applicability to the fields of medicine, agriculture, and biotechnology.

2. Description of the Related Art

The field of spectroscopic analysis seeks, among other characteristics, the configuration of molecules of interest. A molecule often studied is the protein and a configuration of interest is its three dimensional structure. As those in the art recognize, a protein exhibits a specific three-dimensional structure which is critical to activity and function. That three-dimensional structure (also known as the native or folded state) is sensitive to a variety of factors, such as pH, temperature, pressure, or the presence of a denaturant such as urea.

Spectroscopic analysis of proteins is made possible by a protein's ability to absorb light over a wide spectrum and to re-emit it in a characteristic fashion as well as the change in absorbance and emission due to a perturbation of the structure. The three most popular modes of spectroscopic analysis today are based on the absorbance/emission of visible light (the absorbance spectrum), differential absorbance of polarized light (circular dichroism), and fluorescent light. All three modes are sensitive to the three-dimensional structure of a protein. For example, fluorescence emission intensity can be used to gauge the change of molecular configuration as function of some parameter expected to effect the stability of the test molecule. As noted above, this parameter might be pH, some denaturant such as urea, or an extensive property of the system such as temperature or pressure. Practitioners have also used the ellipticity signal at 222 nanometers from circular dichroism ($\theta_{222}$, CD) to estimate the extent of unfolding in proteins having a significant α-helical content.

Nonetheless, each of these methods suffers in adequately testing the proportions of folded state. Fluorescence intensity analysis is highly temperature sensitive. Fluorescence analysis depends on the assumption that the magnitude of a spectroscopic signal at one wavelength will remain a constant function of whether the molecule is in its folded or unfolded form. Thus, the analysis requires that two constant signals exist, one for each form, and that each constant signal be independent of the variation of the perturbing parameter. If this does not occur, as is the case when temperature is the perturbing factor, a correction must be applied. One correction commonly applied is based on Taylor series expansions of unknown functions multiplied by an exponentially declining temperature term, E. A. Permyakov, *The Luminescent Spectroscopy of Proteins* (CRC Press 1993) at pp. 99–107. Although some in the art assert that protein structure as a result of heat denaturation can be studied on a quantitative basis using data so corrected, such data frequently yields coefficients which predict infinite emission intensities in the temperature range from 0° C. to 100° C. Thus the method is often not as reliable as desired over the important temperature range which includes both cold and heat denaturation.

Another important method for determining the denaturation of the protein structure, or extent of exposure of fluorophores to the environment external to the protein, is fluorescence quenching, Joseph Lakowicz, *Principles of Fluorescence Spectroscopy* (Plenum Press 1983) at pp. 279–284. In this method the protein is exposed to varying levels of a quencher such as iodide which cannot interact with fluorophores buried in the protein interior. The percentage of exposed fluorophores can then be calculated using the Stern-Volmer equation:

$$\frac{F_0}{\Delta F} = \left(\frac{1}{f_a} * \frac{1}{K_{Sv}} * \frac{1}{[Q]}\right) + \frac{1}{f_a},$$

where $F_o$ is initial fluorescence intensity at the test wavelength at zero concentration of quencher Q, $\Delta F$ is the initial fluorescence intensity minus the fluorescence intensity at a given concentration of quencher, $f_a$ is the fraction of initial fluorescence accessible to the quencher, $K_{SV}$ is the Stern-Volmer constant, and [Q] is the concentration of quencher Q. However, this cannot easily be related to the percent of protein unfolded because it provides no information about the spectral characteristics of the unquenched fluorophores. Thus, if a protein has two domains, which can be referred to as A and B, with the same number of buried fluorophores, then A may heat denature at a lower temperature than B, but B may cold denature at a higher temperature than A. In this case the Stern-Volmer analysis will show that the protein appears to be increasing the percentage of exposed fluorophores at low temperature and the percent increased exposure could be scaled, using interpolation or normalization techniques, between the initial value and the heat denatured value to estimate a percent of unfolded protein. But, in fact, a different part of the protein would be unfolding.

In the case of $\theta_{222}$ measurements of proteins, one must assume that the shift at that wavelength or the change in signal accurately reflects the helical content of the protein, that the change in helical content reflects accurately the fraction of unfolded protein, and that the protein domain which is unfolding is where the helices are.

It has been generally accepted for quite some time that the helical signal depends strongly on the length of the helices even when total helical content is constant, Y. H. Chen, et al., *Biochemistry* 13:3350 (1974). Also, helices are often quite stable at low temperature as shown by J. M. Scholtz et al., *Proc. Natl. Acad. Sci.*, USA 88:2854 (1991). Thus low temperature tertiary unfolding may leave helical secondary structures intact and the helices may appear longer, i.e., have larger magnitude CD signals, such that the secondary structure may appear even more unlike the denatured state than that from the protein at physiological temperatures. Under these circumstances, $\theta_{222}$ measurements will appear to indicate increasing stability of the protein, an erroneous conclusion.

Thus, there is a need in the art for a spectroscopic analysis that minimizes dependence on the independently varied parameter, such as temperature such that it need not rely on corrections and assumptions that cannot be substantiated. Moreover, there is a need for an analysis that can be used simultaneously with several of the common modes of spectroscopy presently in use.

SUMMARY OF THE INVENTION

To fulfill the above needs, it is an object of the present invention to provide a method for determining the respective fractions of a folded form and an unfolded form of a molecule in solution, in order to estimate a fraction of an unfolded form of a molecule in solution and to determine apparent free energy of a conversion reaction between a folded form and an unfolded form of a molecule in solution.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

Accordingly, to achieve the above object, the present invention, as embodied and broadly defined herein, provides a method of determining the respective fractions of a folded form and an unfolded form of a molecule in solution using differential spectral topographic analysis (DISTA), comprising summing absolute differences in topography between each of two reference spectra and a sample spectrum taken at different magnitudes of at least one perturbation parameter, plotting curves of the sums versus the at least one perturbation parameter, and quantitatively estimating the degree to which the molecules appear similar to folded or unfolded forms of the molecules.

According to another object of the invention, the present invention as embodied and broadly defined herein, provides a method of estimating a fraction of an unfolded form of a molecule in solution, comprising calculating DISTA values for a test spectrum taken at different magnitudes of at least one perturbation parameter, and scaling the DISTA values linearly between values for a pure folded form of the molecule and a pure unfolded form of the molecule to obtain an estimate of the fraction of the unfolded form of the molecule.

According to another object of the invention, the present invention as embodied and broadly defined herein, provides a method of determining apparent free energy of a conversion reaction between a folded form and an unfolded form of a molecule in solution, this method comprising summing absolute differences in topography between each of two reference spectra and a sample spectrum taken at different magnitudes of at least one perturbation parameter to obtain DISTA values, scaling the DISTA values linearly between values for a pure folded form of the molecule and a pure unfolded form of the molecule to obtain an estimate of the fraction of the unfolded form of the molecule, and converting the estimate of the fraction of the unfolded form of the molecule to an estimate of the free energy of unfolding.

According to another object of the invention, the present invention as embodied and broadly defined herein, provides a method of determining the respective fractions of a folded form A and unfolded form B of a molecule in solution, this method comprising the steps of (a) recording two reference spectra, one for each of the forms A and B, (b) normalizing both reference spectra to a topographical space such that the values of the normalized spectra are substantially dependent on the molecular configuration of the molecule of interest, (c) recording test spectra periodically in response to variation in at least one perturbation parameter selected from a group including temperature, pressure, pH, presence of a stabilizer, presence of a ligand, electromagnetic radiation, magnetic field, gravitational field, and presence of a denaturant, (d) normalizing each spectrum such that the values of the normalized spectra are substantially dependent on molecular configuration, and (e) calculating a DISTA value for each test spectrum using the equation:

$$\sum_{\lambda i} |S_{\lambda i r} - S_{\lambda i t}|$$

where $S_{\lambda i r}$ is the normalized reference signal at wavelength $\lambda_i$, $S_{\lambda i t}$ is the normalized test signal at $\lambda_i$ and the sum is over all $\lambda_i$.

According to another object of the invention, the present invention as embodied and broadly defined herein, provides a method of determining the fraction of secondary structure lost in a molecule of interest in solution, comprising recording Far-UV CD reference spectra for a folded form and an unfolded form of the molecule, recording Far-UV CD test spectra as at least one perturbing parameter is systematically varied, normalizing each spectra by converting to ellipticity, calculating DISTA values for the test spectra, and calculating the fraction of secondary structure lost, $F_u$, using the equation:

$$F_u = \frac{D_s - D_{r2}}{D_{r1} - D_{r2}},$$

where $D_s$ is the sample DISTA signal, $D_{r1}$, is the reference signal of greater magnitude, and $D_{r2}$ is the reference signal of lesser magnitude.

According to another object of the invention, the present invention as embodied and broadly defined herein, provides a method of measuring a change from a first configuration to a second configuration in a physical configuration of a system of interest, comprising calculating DISTA values for test spectra by summing absolute differences in topographic values between each of two reference spectra representing the first and second configurations of the system of interest and a sample spectrum taken at different magnitudes of at least one perturbation parameter, plotting each sum versus the at least one perturbation parameter to create a DISTA curve, and proportionally scaling the DISTA values at a value of interest of the perturbation parameter between known reference values for the first and second configurations of the physical configuration of the system of interest to obtain an estimate of the fraction of conversion to the second configuration of the physical configuration of the system of interest.

BRIEF DESCRIPTION OF FIGURES

The file of this patent contains at least one drawing executed in color. Copies of this patent with color drawings will be provided by the Patent and Trademark Office upon request and payment of the necessary fee.

FIGS. 1A–1I depict the DISTA values plotted against the perturbing parameter from fluorescence spectra for a series of proteins over a temperature range.

FIGS. 2A–2I depict the DISTA from fluorescence spectra for another series of proteins varied over a temperature range.

FIG. 3 depicts the DISTA analysis of cold annealed myoglobin in Far-UV CD.

FIGS. 4A and 4B depict the DISTA analysis of cold annealed myoglobin in Far-UV CD.

DETAILED DESCRIPTION OF THE INVENTION

Figure 5:
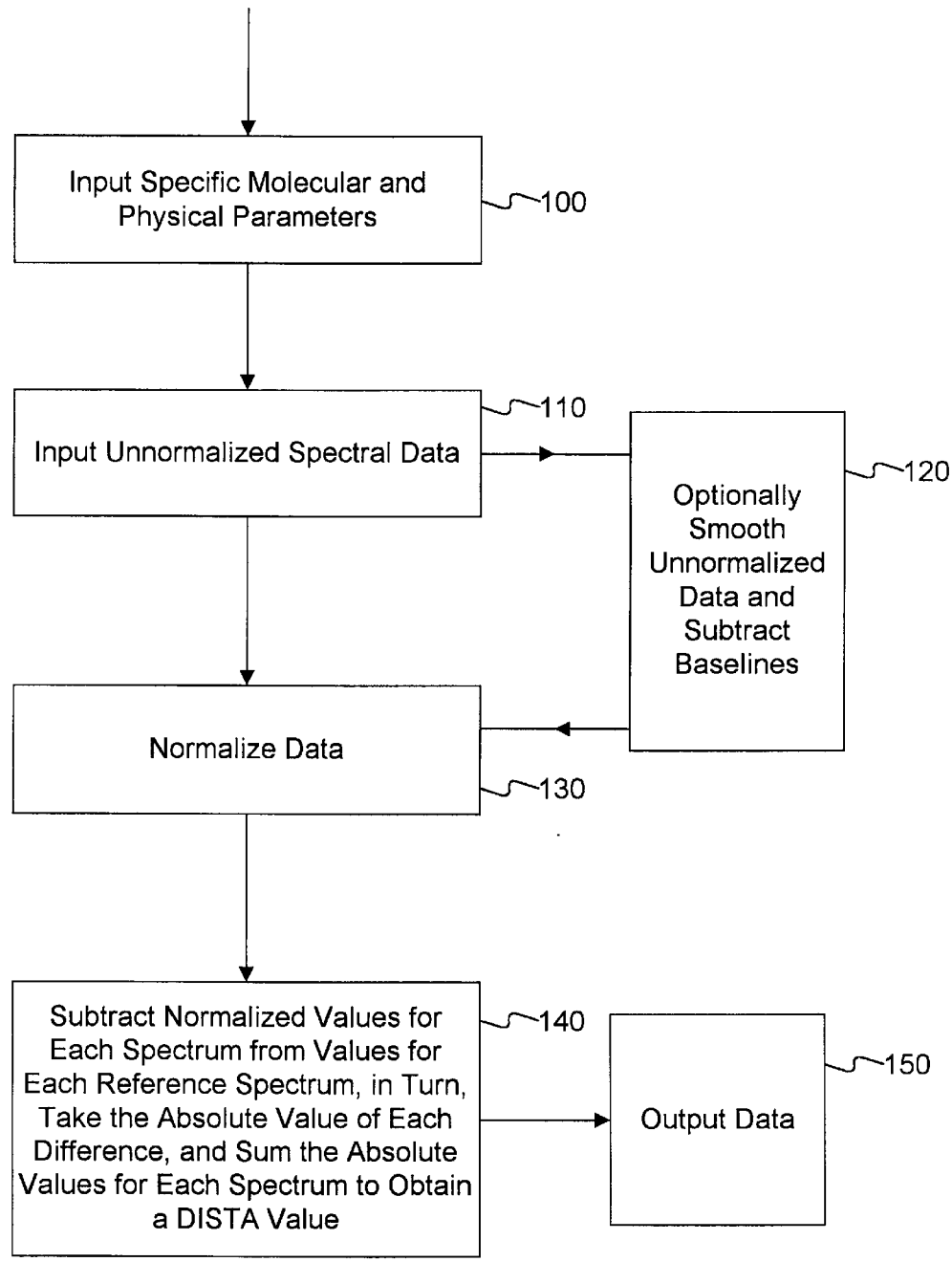
FIG. 5 is a flow chart depicting the calculation of DISTA values.

According to the present invention, and as embodied herein, an analysis to estimate the fraction of folded and unfolded forms of a molecule in solution is provided, wherein the molecule represents an organic or non-organic organized system, including proteins, polymers, biopolymers, and peptides. This method of analysis is based on Differential Spectral Topographic Analysis (DISTA). The DISTA method uses data from the spectral methods known in the art and is based upon the normalization of the spectra to a fixed topographic space, creating a set of spectral forms, and the summation of the absolute differences in topography between one or more such reference spectra and the test spectra taken at different magnitudes of the perturbing parameter. This method allows for an estimate of the fraction of folded and unfolded forms of proteins even if the dependence of the unnormalized signal on the perturbation parameter varies in a complex and mathematically unknown way. As long as this topographic absolute difference signal is essentially zero over the range in which only the pure reference form (whether folded or unfolded) would be expected to exist, then the method can reasonably be used as a quantitative measure of unfolding.

In the practice of the invention, standard spectroscopic methods well known to those of ordinary skill in the art and based on the UV or VIS absorbance spectrum, fluorescence spectrum, and/or Far and Near UV CD spectrum are used. This method is applicable to all spectral methods, and the normalization techniques used for each spectra will vary accordingly, as should be obvious to one of skill in the art. These methods can be used so long as it can reasonably be expected that over a definable range of the perturbing parameter the spectral form is independent of the perturbing parameter. Any perturbation parameter which wouldn't change the topographic signal but would affect the configuration of molecule in an area of interest and would reflect this change in the topographic signal may be used, for example, the perturbing parameter may be temperature, pressure, pH, presence of a stabilizer, presence of a ligand, electromagnetic radiation, magnetic field, gravitational field, or presence of a denaturant. For example, the spectral form can reasonably be expected to be independent of the perturbing parameter of temperature through a range of 20° C. to 50° C. Thus, for many proteins the forms of the UV or VIS absorbance spectrum, fluorescence spectrum, and Far and Near-UV CD spectrum are dependent on molecular configuration and relatively insensitive to temperature over certain temperature ranges. This is illustrated over temperature ranges of widths $\geq$20° C. for a number of proteins in FIGS. 1 through 4, and can be used at any temperature as long as it is possible to optically measure.

The DISTA method of the invention provides a quantitative measure of the folding nature of the molecule of interest (when using fluorescence or absorbance spectra) or fraction of loss of secondary structure (when using Far-UV CD spectra) by the following steps:

(1) Recording two reference spectra, one of the appropriate pure form A (e.g., the folded or native form) of a molecule, the other of the complementary pure form B (e.g., the unfolded form of the molecule).

(2) Normalizing both spectra to the topographic space (0,1) in fluorescence or absorption spectra. This is accomplished for each spectrum separately by dividing all values in each spectrum by the absolute value of the maximum magnitude value (fluorescence or absorbance spectra), or by integrating the partial area of the curve from the starting value to each of the intermediate values and subsequently dividing by the entire area under the spectral curve. This latter method more accurately represents the statistical distribution of excited state energies and is thus more rigorous. In practice there is rarely any significant difference in the predictions of these two alternatives and the first is calculationally faster. If the spectra being analyzed are CD spectra, then they are normalized by converting to ellipticity, a standard procedure for those skilled in the art.

(3) Test spectra are then recorded periodically as one or more perturbing parameters, such as temperature, pressure, pH, presence of a stabilizer, presence of a ligand, electromagnetic radiation, magnetic field, gravitational field, or presence of a denaturant are systematically varied. The variation of these perturbing parameters is well within the skill of those in the art.

(4) Each spectrum is subsequently normalized by dividing all of its values by the absolute value of that spectrum's maximum magnitude value (when fluorescence or absorbance is used), or by converting to ellipticity (when CD is used).

(5) The DISTA value for the test spectrum is then calculated as:

$$\left[\sum_{\lambda i} |S_{\lambda ir} - S_{\lambda it}|^n \right]^{1/n}$$

where n is a transform scaling exponent generally equal to one (1), $S_{\lambda ir}$ is the normalized reference signal at wavelength $\lambda_i$ (the wavelength of measurement which is varied systematically from a minimum to a maximum), $S_{\lambda it}$ is the normalized test signal at $\lambda_i$ and the sum is over all $\lambda_i$. The difference between the test spectra and the reference spectra may also be calculated using exponential values of the signals different from one, i.e., n$\approx$1, depending upon the physical system being tested. For protein unfolding, the sum of the absolute difference is the preferred method.

(6) The DISTA values (for fluorimetric, absorbance, and CD) are then scaled linearly between the values for the two pure forms, folded and unfolded, and the estimate of the fraction unfolded, $F_u$, is determined by the equation:

$$F_u = \frac{D_s - D_{r2}}{D_{r1} - D_{r2}}$$

where $D_s$ is the sample DISTA signal, $D_{r1}$ is the reference signal greater in magnitude, and $D_{r2}$ is the reference signal lesser in magnitude.

(7) The estimate of the fraction unfolded, $F_u$, can then be directly converted to an estimate of free energy of unfolding using: $\Delta G = -RT\text{Log}(K)$, where $\Delta G$ is the free energy of the reaction folded to unfolded, R is the gas constant, T is the absolute temperature, and K is the mass action constant of the reaction:

$$K = \frac{[B]}{[A]},$$

where the [A] is the concentration of folded form of the molecule of interest and [B] is the concentration of unfolded form of the molecule of interest. If the spectrum analyzed is Far-UV CD, then $F_u$ represents fraction of secondary structure lost. This may not necessarily reflect the extent of tertiary unfolding, but is of primary concern in establishing whether the refolded species are really native state and in establishing the fraction of secondary structure lost, if any. Quantification of the continuous loss of secondary structure with time and as a function of protein concentration is shown in FIGS. 3, 4A, and 4B.

As embodied in FIGS. 1 and 2, an analysis has been performed on various proteins in aqueous solutions over a wide temperature range. The sum of absolute differences at each wavelength between a sample spectrum and each of two reference spectra (fully native or folded, and fully denatured or unfolded, respectively) were calculated and used to draw two curves of Σ (differences with each reference spectrum) vs. temperature. These allow quantitative estimation of the degree to which the protein appears similar in structure to a native or denatured form. If the sums fall between the values of the reference spectra, they can be scaled to yield an estimate of fraction unfolded.

For FIGS. 1A–1I and 2A–2I, each sample was prepared and then the sample was split in half on the bench. The first half of the sample was run immediately, and the second half of the sample was run after the first half was complete. The following example completely describes the development of a representative set of DISTA statistics as done in FIGS. 1A–1I and 2A–2I, and their use to calculate a fraction of protein unfolded and the free energy of unfolding. The example below describes general preparation of the samples using lysozyme at pH 4.8 as illustrated in FIG. 1A. Calculation of DISTA values in curves 3–6 (black, green, dark blue, and light blue curves, respectively) at 0° C. will be illustrated.

EXAMPLE 1

First, the sample was dissolved in 10 millimolar acetate buffer, pH 4.8, at room temperature at concentration 0.23 mg/ml. The protein was allowed to equilibrate in this state for at least 24 hours. The solution was then divided into two equal portions. The first portion was inserted in the fluorimeter, and cooled at 0.3° C./min to a temperature of −10° C. The computer controlled cooling bath was then instructed to begin heating the sample to a temperature in excess of 100° C. at the same low rate of temperature change. Throughout this procedure, as the temperature gradually increased, fluorescence emission spectra (320 nm–365 nm with excitation at 280 nm) were being recorded at a rate of two or three per minute. After recooling of the sample chamber to room temperature the second portion of the sample held at room temperature was then inserted into the fluorimeter and was immediately warmed at 0.3° C./min to a temperature above 100° C. while fluorescence emission spectra were being recorded at a rate of two or three per minute.

After all spectra were recorded, a high temperature fluorescence emission spectrum of a sample maintained at room temperature before this test was chosen as a reference such that it could reasonably be assumed that the protein is essentially entirely in a heat denatured (unfolded) form at the chosen temperature. In this instance, the spectrum at 95° C. was chosen. The maximum of emission was found to be close to 350 nm. Then the values of emission at all wavelengths in this spectrum, ranging from 320 nm to 365 nm were divided by this aforementioned maximum. The values so obtained range in magnitude from 0 to 1 and they are the normalized spectrum at 95° C. The same process was repeated utilizing the spectrum at 35° C. of a sample maintained at room temperature before this test, this value having been chosen because the evidence from a variety of techniques indicates that 35° C. is a temperature at which the protein, in physiological solution, would reasonably be expected to be essentially entirely in the native (folded) form. In this case, however, the maximum of emission to be used as the divisor was close to 335 nm. To develop the four DISTA data points for 0° C., the next step was to repeat the normalization process for the spectrum taken at 0° C. during the initial cooling of the protein solution (lower black curve 3). In this case, the maximum of emission was found to be at a wavelength between approximately 335 nm and 340 nm. After this spectrum was normalized by dividing all of its values by its maximum emission value, the sum of absolute differences was calculated with respect to the normalized reference spectrum recorded at 35° C. To do this, the normalized value of the native reference at each wavelength was subtracted from the normalized value of the 0° C. spectrum at each matching wavelength, e.g., the reference value at 320 nm minus 0° C. value at 320 nm, the reference value at 325 nm minus 0° C. value at 325 nm, etc. The absolute value of each of these differences is equal to the positive value of each difference. The sum of these absolute values over all of the wavelengths at which measurements were taken constituted the DISTA value for the 0° C. spectrum during cooling (curve 3, black if in color). The other three values at 0° C. as shown in FIG. 1A for lysozyme pH 4.8 were calculated in the same fashion except for the following:

a) the reference spectrum used to calculate the 0° C. data point in the upper curve 6 (light blue if in color) was the normalized 95° C. reference spectrum instead of the 35° C. normalized reference spectrum;

b) the 0° C. data point in curve 5 (dark blue if in color) used the normalized spectrum from the sample recorded during rewarming instead of recooling, and the normalized 95° C. reference spectrum instead of the 35° C. normalized reference spectrum was used; and c) the 0° C. data point in curve 4 (light green if in color) used the normalized spectrum from the sample recorded during rewarming instead of cooling.

Once the entire set of DISTA values over the temperature range of interest was calculated the fraction unfolded and free energy of unfolding could be calculated for any temperature of interest. The calculation for 0° C. is as follows. The maximum DISTA value for the curves referencing the high temperature state is 0.8 units near 40° C. At 0° C., the value is 0.6 units, so there is a loss of value of 25% of the full change in value going from native state (folded form) to high temperature denatured state (unfolded form). Thus, the estimate is that the protein has a ratio of B (unfolded) to A (folded) of [0.25]/[0.75]. From this fraction, the apparent free energy of the reaction A⇌B is generally derivable from the equation:

$$\Delta G = -RT \, \text{Log}(K).$$

In the FIGS. 1A–2I, curves 1 and 2 (or the red and magenta curves, respectively, if in color, red representing a warming only curve referenced to the denatured state and magenta representing a warming only curve referenced to the native state) represent the results the first half of the sample, and curves 3, 4, 5, and 6 (or the black, green, dark blue, and light blue curves if in color, black representing initial cooling referenced the native state, green representing rewarming referenced to the native state, dark blue representing rewarming referenced to the denatured state, and light blue representing cooling referenced to the denatured state) represent the test results of the other half of the sample. In each of the FIGS. 1A–2I, the curve number and color correspond to the same portion of the curve. Therefore, curves 1 (red if in color) represent a warming only curve, curves 2 (magenta if in color) represent a warming curve, curves 3 (black if in color) represent initial cooling, curves 4 (green if in color) represent rewarming, curves 5 (dark blue if in color) represent rewarming, and curves 6 (light blue if in color) represent cooling. Points 7 and 8 represent the chosen reference points at which by definition the reference spectra and test spectra are the same. In each of the figures, it can be noted that curve 4 (green) closely follows curves 2 and 3 (magenta and black), and curve 5 (dark blue) closely follows curves 6 and 1 (light blue and red). The difference between the curve 4 (green) and curves 2 and 3 (magenta and black), and curve 5 (dark blue) and curves 6 and 1 (light blue and red) represents hysterisis, showing that there have been permanent changes in the molecule from the cooling process and subsequent reheating.

If a measurable fraction, i.e., a fraction sufficient to change the scope of the test, of molecules converts from form A to form B or vice versa, the two complementary DISTA curves will depart from the baseline as mirror images, i.e., if one were to reverse curves 2, 3, and 4 (magenta, black, and green), or look at them in a mirror and compare them with curves 1, 5, and 6 (red, dark blue, and light blue), it would be seen that the curves match up, that is, they are essentially mirror images of one another. If the curves depart from baseline largely asymmetrically as in the proteins shown in FIGS. 1E, 1F, 1G, 1I, 2D, and 2G, that is an indication that the conversion is to a form distinct from both A and B. However, if largely symmetric as in the proteins shown in FIGS. 1A, 1B, 1C, 1D, 2A, 2B, 2C, 2E, 2H, and 2I, the DISTA signals can be construed as representing fractions of each of the two forms (by proportionally scaling them between the values for the pure forms) and the apparent free energy of the reaction A⇌B is then generally derivable from:

$$\Delta G = -RT\mathrm{Log}(K)$$

where $\Delta G$ is the free energy of the reaction folded to unfolded, R is the gas constant, T is the absolute temperature, and K is the mass action constant of the reaction:

$$K = \frac{[B]}{[A]}.$$

As discussed earlier, the method for determining the extent of exposure of fluorophores to the environment external to the protein known as fluorescence quenching cannot easily be related to the percent of protein unfolded because it provides less information about the spectral characteristics of the unquenched fluorophores. In the DISTA method, the contributions of essentially all of the fluorophores are taken into account, so unfolding of a domain at low temperature different from the domain that unfolds at high temperature would produce an increase in the difference signal at low temperature relative to both the native state and high temperature denatured forms (curve asymmetry). This is illustrated in several of the figures, such as in Lactoferrin in FIG. 1F and in Ovalbumin in FIG. 2G. The Stern-Volmer analysis can be used, however, to confirm that, even in some cases where the low temperature DISTA curves are substantially asymmetric, it is unfolding that is occurring by showing that the fraction of quenchable fluorophores increases.

Because helices are often quite stable at low temperature (J. M. Scholtz et al.), low temperature tertiary unfolding may leave helical secondary structures intact and the helices may appear longer, i.e., have CD signals of larger magnitude, such that the secondary structure may appear even more unlike the heat denatured state than it does from the protein at physiological temperatures. Under these circumstances, $\theta_{222}$ measurements will appear to indicate increasing stability of the protein. Concurrently DISTA performed on data sets from Far-UV CD will yield substantially asymmetric curves which will be evidence that the low temperature secondary structures are different from the two reference states, but if the amount of secondary structure decreases as a result of a second perturbation such as protracted exposure of the protein to low temperature, then DISTA will measure the extent of secondary structure loss even if the structures are not helices and the curves are asymmetric. FIGS. 3, 4A, and 4B represent examples where the DISTA analysis has used Far-UV CD spectra rather than fluorescence spectra. FIGS. 3, 4A and 4B show in Far-UV CD DISTA for helical data from myoglobin annealed at 0° C. for extended periods. Curve 12 in FIG. 3 represents myoglobin annealed at 0° C. for 45 days in a concentration of 0.1 mg/ml, curve 14 represents myoglobin annealed at 0° C. for 45 days in a concentration of 0.2 mg/ml, curve 16 represents myoglobin annealed at 0° C. for 45 days in a concentration of 0.3 mg/ml, and curve 18 represents myoglobin annealed at 0° C. for 45 days in a concentration of 0.6 mg/ml. Curve 20 in FIGS. 4A and 4B represents myoglobin annealed at 0° C. for 15 days in concentration of 0.23 mg/ml, curve 22 represents myoglobin annealed at 0° C. for 14 days at 2.3 mg/ml then diluted 1:10 to a concentration of 0.23 mg/ml just before measurement, and curve 24 represents a relaxed myoglobin sample 3 days at room temperature in concentration of 0.23 mg/ml.

As an example, a complete description of the development of a representative set of DISTA statistics based on Far-UV CD and their use to calculate the fraction of secondary structure lost follows using the data in FIGS. 4A and 4B for myoglobin pH 4.8. We will illustrate the calculation of the DISTA values at 30° C.

EXAMPLE 2

First, the sample was dissolved at room temperature in 10 millimolar acetate buffer to a concentration of 2.3 mg/ml. The protein was allowed to equilibrate in this state for 72 hours. The solution was then divided into three equal portions.

The first portion (red curve 24) was diluted to 0.23 mg/ml and inserted in the CD at room temperature and immediately warmed at 0.3° C./min to a temperature above 100° C. while spectra were being recorded at a rate of two to three per minute.

The second portion (blue curve 20) was diluted to 0.23 mg/ml, then placed on ice and held for 15 days at 0° C. It was then placed in the CD at 0° C. The cooling bath was then instructed to begin heating the sample to a temperature in excess of 100° C. at the same low rate of 0.3° C./min as for portion one. Throughout this procedure Far-UV CD spectra were being recorded at a rate of two to three per minute. After the sample was heated to the maximum temperature, it was rapidly recooled and removed from the CD.

The third portion (green curve 22) was undiluted at 2.3 mg/ml also placed on ice and held for 14 days at 0° C. After that it was diluted to 0.23 mg/ml and immediately placed in the CD at 0° C. The cooling bath was then instructed to begin heating the sample to a temperature of 68° C. at the same low rate of 0.3° C./min as for the first portion. Throughout this procedure Far-UV CD spectra were being recorded at a rate of two to three per minute. After the sample was heated to the maximum temperature it was recooled at the same rate as warming while additional spectra were recorded.

After all spectra were recorded, they were normalized by converting to ellipticity using the standard equation:

$$\theta = 0.0001 * (m°) * (MW)/(C * r * L)$$

where $\theta$ is in units of $10^{-3}$ deg cm$^2$ decimol$^{-1}$, m° is the actual CD instrument result in millidegrees, MW is the molecular weight of the protein in daltons, C is protein concentration in mg/ml, r is the number of amino acid residues per molecule, and L is the path length in cm.

A high temperature CD spectrum was chosen as a reference such that it could reasonably be assumed that the protein is essentially entirely in a heat denatured (unfolded) form at the chosen temperature. In this case, the spectrum of the material relaxed at room temperature and then heated to 90° C. was chosen. For the native state reference the same process was repeated utilizing the spectrum of material maintained at 30° C. prior to the test. This was chosen because evidence from a variety of techniques indicates that 30° C. is a temperature at which the protein, in physiological solution, would be expected to be essentially entirely in the native (folded) form.

To develop the estimate of percent loss of secondary structure in the cold annealed samples (the second and third portions), a computer program has been developed to calculate DISTA values as follows. The sum of absolute difference with respect to the normalized native reference spectrum recorded at 30° C. are calculated. To do this, the normalized value of the native reference at each wavelength was subtracted from the normalized value of the 30° C. spectrum at each matching wavelength, e. g., the reference value at 240 nm minus the 30° C. value at 240 nm, the reference value at 239 nm minus the 30° C. value at 239 nm, etc. The absolute value of each of these differences is equal to the positive value of each difference. The sum of these absolute values over all of the wavelengths at which measurements were taken constituted the DISTA value for the 30° C. spectrum in each sample.

Once the entire set of values over the temperature range of interest was calculated the fraction of secondary structure lost could be calculated for any temperature of interest. The calculation for the fraction of secondary structure lost for 30° C. was performed as follows. The DISTA value for the reference curve at 90° C. is 2600 units. At 30° C. the value is 0 units. For the sample portion annealed 15 days at 0.23 mg/ml the value at 30° C. is 350 units or 13% of the full change in value going from native to high temperature denatured state (from 30° C. to 90° C.). Thus, the estimate is that for the protein annealed at 0° C. at this concentration, about 13% of the secondary structure which is labile to heat denaturation has been lost.

FIG. 5 describes the flow chart for a computer program calculating the important parameters in the DISTA method of spectral analysis. In the first step 100, the specific molecular and physical parameters are input to the system by the investigator. This would include such data as the molecular weight of a protein, the concentration of the protein in the solution, the name of the file wherein unprocessed spectral data is stored, and other parameters that will be necessary in the calculation of the DISTA statistics. In the next step 110, the program inputs the unnormalized spectral data as it has been produced by the analyzing machine. It may be a circular dichroic measuring device, an absorption spectrophotometer, spectrofluorimeter or other similar device. In the next step 120 which is optional, the data may be smoothed by various classical smoothing algorithms to eliminate noise components. In addition, if there are baselines that indicate systematic noise parameters such as scattering in a spectrofluorimeter they can be subtracted at this step from the unnormalized spectral data. In the next step 130, the data is normalized. The algorithm for normalizing the data will depend on the appropriate methodology for each spectral measuring type. As an example, in fluorimetry the total area under the spectral curve will be calculated, then the partial areas from the starting wavelength to each in turn of each of the intermediate wavelengths will be calculated, and the partial areas so calculated will be then be divided by the total area to get a series of partial normalized areas. Alternatively, also in fluorimetry, the emission intensities of each wavelength will be analyzed, the maximum intensity will be determined. The maximum intensity is then divided into each of the intensities in each spectrum to produce a normalized intensity spectrum. In the next step 140, the DISTA values for each spectrum will be calculated. Two spectra have been chosen to represent the values for the test molecules wholly in form A or wholly in form B, and the subtraction will be of all of the other normalized spectral values in turn for each normalized spectrum from each of the normalized reference spectra individually. Thus, if one of the reference spectra was recorded at 35° C. with temperature as the perturbing parameter, then the DISTA value for the 60° C. spectrum will be calculated by this program by taking each of the normalized values at 60° C. for each wavelength recorded at 60° C. subtracted from the value at the same wavelength in the normalized 35° C. spectrum. The program will then calculate the positive value of the subtraction and sum all of those positive values to give the DISTA value for the 60° C. spectrum versus the 35° C. spectrum. This is the DISTA value calculated by the program. In the final step 150, the program outputs the data to disk or stores it in an array in memory for use to calculate the fraction unfolded where that is appropriate.

Figure 6:
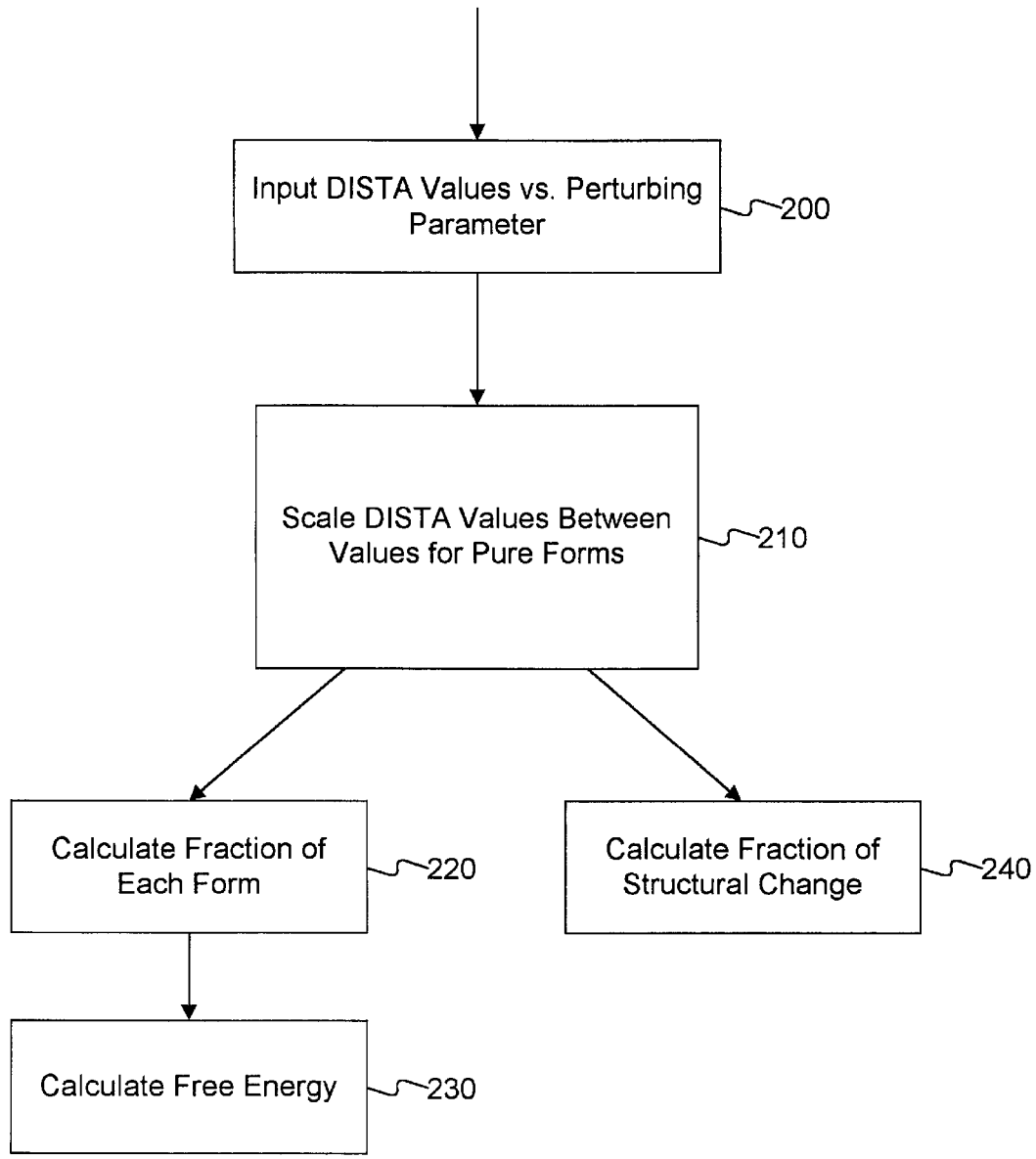
FIG. 6 is a flow chart depicting the calculation of apparent free energy and fraction of structural change.

FIG. 6 shows a flow chart for the calculation of fraction unfolded, where the DISTA value at any given value of the perturbing parameter is scaled between the two limiting values. In the first step 200, the DISTA value vs. perturbing parameter is input. In the second step 210, DISTA values are scaled between values for pure forms of the molecule of interest. As an example, if the value at 35° C. is a reference for a particular protein, and temperature is the perturbing parameter, then the DISTA value at 35° C. of the 35° C. reference spectrum is 0, and the value at 90° C. (where the protein is heat denatured) might be 1.5 units. If at 60° C. it is 0.75 units, i.e., the value is scaled half way between the 35° C. value and the 90° C. value, that would then indicate that the fraction of the high temperature form present at 60° C. is 0.5 and that would be the fraction unfolded parameter calculated from the DISTA data (step 220). In those cases where fraction unfolded can be calculated, step 230 is performed and the free energy can then be calculated directly in the same program by multiplying the logarithm of (the ratio of fraction unfolded to fraction folded) times the absolute temperature in kelvin times the gas constant R, which equals the negative of the Gibbs free energy of conversion of the folded form to the unfolded form. In cases where the test measurement would not be expected to give an accurate estimate of the fraction unfolded, such as some cases of secondary structure breaking measured by Far-UV CD, the DISTA analysis can still be used as a valuable tool. For example, the percentage of secondary structure conversion at certain levels of perturbation parameters (e.g. temperature) can be estimated by scaling the DISTA value as described above (step 220) within the two reference states at two different levels of the perturbing parameters (step 240).

Although the conversion from one form to another of a given entity of interest has been expressed as a determination of protein unfolding, this method is equally applicable to other entities of interest. Given any physical configuration of a system of interest, such as a molecule, an aggregation of molecules, a liquid crystal structure, or a physical surface, a perturbing parameter of interest, where the physical configuration may change structure in ways of interest to the investigator, and any kind of signal from a measuring device which impinges on a surface of the configuration and whose signal can be transformed such that the signal is only responsive to the entity of interest and is substantially independent of the perturbing parameter, DISTA calculations may be used to measure the change from conversion of the entity from one configuration to another.

Having now fully described the invention, it will be apparent to one of ordinary skill in the art that many changes and modifications can be made thereto without departing from the spirit or scope of the invention as set forth herein. The appended claims are not intended to be limiting.

What is claimed is:

1. A method of determining the respective fractions of a folded form and an unfolded form of a molecule in solution, comprising:

recording two reference spectra for each of a folded form and unfolded form of the molecule;

normalizing the reference spectra to a fixed topographic space;

summing absolute differences in topographic values between each of two reference spectra representing a folded form and an unfolded form of the molecule and a sample spectrum taken at different magnitudes of at least one perturbation parameter, wherein said sample spectrum is normalized to said fixed topographic space;

plotting each sum versus the at least one perturbation parameter to create a differential spectral topographic analysis curve; and quantitatively estimating the degree to which the molecule appears similar to a folded or unfolded form of the molecule by using data points chosen from the curve and scaling these points between known reference values for folded and unfolded forms of the molecule.

2. The method of claim 1, wherein the at least one perturbation parameter is chosen from temperature, pressure, pH, presence of a stabilizer, presence of a ligand, electromagnetic radiation, magnetic field, gravitational field, and presence of a denaturant.

3. The method of claim 1, further comprising:

recording test spectra periodically in response to a variation in the at least one perturbation parameter for comparison to reference spectra of the molecule of interest.

4. The method of claim 1, wherein the step of summing includes calculating a DISTA value for each test spectrum using the equation:

$$\left[\sum_{\lambda i} |S_{\lambda ir} - S_{\lambda it}|^n\right]^{1/n}$$

where n is a transform scaling exponent, $S_{\lambda ir}$ is a normalized reference signal at wavelength $\lambda_i$, $S_{\lambda it}$ is a normalized test signal at $\lambda_i$, and the sum is over all $\lambda_i$.

5. The method of claim 1, wherein the molecule is an organic or non-organic organized system.

6. The method of claim 1, wherein the at least one perturbation parameter is temperature variable over a range of interest.

7. The method of claim 1, wherein substantially asymmetric curves indicate a form of the molecule other than its reference folded or unfolded forms; and wherein substantially symmetric curves indicate respective fractions of its reference folded and unfolded forms of the molecule.

8. A method of estimating a fraction of an unfolded form of a molecule in solution, comprising:

calculating DISTA values for test spectra taken at different magnitudes of at least one perturbation parameter; and proportionally scaling the DISTA values between known reference values for a folded form of the molecule and an unfolded form of the molecule to obtain an estimate of the fraction of the unfolded form of the molecule.

9. The method of claim 8, wherein the DISTA value is calculated using the equation:

$$\left[\sum_{\lambda i} |S_{\lambda ir} - S_{\lambda it}|^n\right]^{1/n}$$

where n is a transform scaling exponent, $S_{\lambda ir}$ is a normalized reference signal at wavelength $\lambda_i$, $S_{\lambda it}$ is a normalized test signal at $\lambda_i$, and the sum is over all $\lambda_i$.

10. The method of claim 9, wherein n=1.

11. The method of claim 9, wherein n≠1.

12. The method of claim 8, wherein the DISTA values are scaled using the formula:

$$F_u = \frac{D_s - D_{r2}}{D_{r1} - D_{r2}}$$

where $D_s$ is the sample DISTA signal, $D_{r1}$ is the reference signal of greater magnitude, $D_{r2}$ is the reference signal of lesser magnitude, and $F_u$ is the estimate of the percentage of molecule in the unfolded form expressed as a fraction.

13. A method of determining apparent free energy of a conversion reaction between a folded form and an unfolded form of a molecule in solution, comprising:

summing absolute differences in topographic values between each of two reference spectra representing a folded form and an unfolded form of the molecule of interest and a sample spectrum taken at different magnitudes of at least one perturbation parameter to obtain DISTA values;

proportionally scaling the DISTA values between known reference values for a folded form of the molecule and an unfolded form of the molecule to obtain an estimate of the fraction of the unfolded form of the molecule; and converting the estimate of the fraction of the unfolded form of the molecule to an estimate of the free energy of unfolding.

14. The method of claim 13, wherein DISTA values are calculated using the equation:

$$\sum_{\lambda i} |S_{\lambda ir} - S_{\lambda it}|$$

where $S_{\lambda ir}$ is a normalized reference signal at wavelength $\lambda_i$, $S_{\lambda it}$ is a normalized test signal at $\lambda_i$, and the sum is over all $\lambda_i$.

15. The method of claim 13, wherein the DISTA values are scaled using the formula:

$$F_u = \frac{D_s - D_{r2}}{D_{r1} - D_{r2}}$$

where $D_s$ is the sample DISTA signal, $D_{r1}$ is the reference signal of greater magnitude, $D_{r2}$ is the reference signal of lesser magnitude, and $F_u$ is the estimate of the percentage of molecule in the unfolded form expressed as a fraction.

16. The method of claim 13, wherein the estimate of the fraction of the unfolded form of the molecule is converted using the equation:

$$\Delta G = -RT \, \text{Log}(K)$$

where $\Delta G$ is the free energy of the reaction folded to unfolded, R is the gas constant, T is the absolute temperature, and K is the mass action constant of the reaction:

$$K = \frac{[B]}{[A]}.$$

17. A method of determining the respective fractions of a folded form A and unfolded form B of a molecule in solution, comprising the steps of:
(a) recording two reference spectra for each of the forms A and B;
(b) normalizing both reference spectra to a topographical space such that the values of the normalized spectra are substantially dependent on the molecular configuration of the molecule of interest;
(c) recording test spectra periodically in response to variation in at least one perturbation parameter selected from a group including temperature, pressure, pH, presence of a stabilizer, presence of a ligand, electromagnetic radiation, magnetic field, gravitational field, and presence of a denaturant;
(d) normalizing each spectrum to the appropriate topographical space; and
(e) calculating a DISTA value for each test spectrum using the equation:

$$\left[ \sum_{\lambda i} |S_{\lambda ir} - S_{\lambda it}|^n \right]^{1/n}$$

where n is a transform scaling exponent, $S_{\lambda ir}$ is the normalized reference signal at wavelength $\lambda_i$, $S_{\lambda it}$ is the normalized test signal at $\lambda_i$ and the sum is over all $\lambda_i$.

18. The method of claim 17, wherein the at least one perturbation parameter is temperature variable over a range of interest.

19. The method of claim 17, wherein substantially asymmetric DISTA curves indicate a form of the molecule other than folded form A and unfolded form B; and
wherein substantially symmetric DISTA curves indicate respective fractions of folded form A and unfolded form B of the molecule.

20. The method of claim 17, wherein the normalizing of reference spectra is accomplished by dividing all values in each spectrum by the absolute value of the maximum value in each spectrum, irrespective of sign.

21. The method of claim 17, further comprising:
(f) plotting the DISTA values versus the at least one perturbation parameter; and
(g) estimating the respective fractions of the folded form A and unfolded form B of the molecule using the DISTA curves.

22. A method of determining the fraction of secondary structure lost in a molecule of interest in solution, comprising:
recording Far-UV CD reference spectra for a folded form and an unfolded form of the molecule;
recording Far-UV CD test spectra as at least one perturbing parameter is systematically varied;
normalizing each spectra by converting to ellipticity;
calculating DISTA values for the test spectra; and
calculating the fraction of secondary structure lost, Fu, using the equation:

$$F_u = \frac{D_s - D_{r2}}{D_{r1} - D_{r2}}$$

where $D_s$ is the sample DISTA signal, $D_{r1}$ is the reference signal of greater magnitude, and $D_{r2}$ is the reference signal of lesser magnitude.

23. A method of measuring a change from a first configuration to a second configuration in a physical configuration of a system of interest, comprising:
calculating a DISTA value for each test spectrum using the equation:

$$\left[ \sum_{\lambda i} |S_{\lambda ir} - S_{\lambda it}|^n \right]^{1/n}$$

where n is a transform scaling exponent, $S_{\lambda ir}$ is the normalized reference signal at wavelength $\lambda_i$ at the value r of the perturbing parameter, $S_{\lambda it}$ is the normalized test signal at $\lambda_i$ at the value of the perturbing parameter t and the sum is over all $\lambda_i$;
plotting at least one sum for at least one value of perturbation parameter t versus said at least one value of the perturbation parameter t to create a DISTA value; and
proportionally scaling the DISTA values at a value of interest of the perturbation parameter between known reference values for the first and second configurations of the physical configuration of the system of interest to obtain an estimate of the fraction of conversion to the second configuration of the physical configuration of the system of interest.

24. The method of claim 23, wherein n=1.

25. The method of claim 23, wherein n≠1.

* * * * *